United States Patent
Verbeke et al.

(10) Patent No.: US 11,229,691 B2
(45) Date of Patent: *Jan. 25, 2022

(54) **VACCINE COMPOSITION AGAINST *CHLAMYDIACEAE* INFECTIONS**

(71) Applicants: CENTRE NATIONAL DE LA RECHERCHE SCIENTIFIQUE (CNRS), Paris (FR); UNIVERSITE PARIS DIDEROT PARIS 7, Paris (FR); INSTITUT NATIONAL DE LA SANTE ET DE LA RECHERCHE MEDICALE (INSERM), Paris (FR)

(72) Inventors: Philippe Verbeke, Paris (FR); Colette Kanellopoulos, Versailles (FR)

(73) Assignees: CENTRE NATIONAL DE LA RECHERCHE SCIENTIFIQUE (CNRS), Paris (FR); UNIVERSITE PARIS DIDEROT PARIS 7, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/884,649

(22) Filed: May 27, 2020

(65) Prior Publication Data
US 2020/0384098 A1 Dec. 10, 2020

Related U.S. Application Data

(63) Continuation of application No. 15/747,489, filed as application No. PCT/EP2016/068079 on Jul. 28, 2016, now Pat. No. 10,695,416.

(30) Foreign Application Priority Data

Jul. 28, 2015 (FR) ...................... 1557211

(51) Int. Cl.
*A61K 39/118* (2006.01)
*A61P 31/04* (2006.01)
*G01N 33/569* (2006.01)
*A61K 39/00* (2006.01)

(52) U.S. Cl.
CPC .......... *A61K 39/118* (2013.01); *A61P 31/04* (2018.01); *G01N 33/56927* (2013.01); *A61K 2039/521* (2013.01); *G01N 2800/26* (2013.01)

(58) Field of Classification Search
None
See application file for complete search history.

(56) References Cited

FOREIGN PATENT DOCUMENTS

| WO | 92/00096 A1 | 6/1991 |
| WO | 91/41889 A1 | 4/1997 |
| WO | 2011/086134 A1 | 7/2011 |

OTHER PUBLICATIONS

Lu et al. 2002 (GM-CSF transgene-based adjuvant allows the establishment of protective mucosal immunity following vaccination with inactivated Chlamydia trachomatis; The Journal of Immunology169: 6324-6331). (Year: 2002).*
Campos et al. 1995 (A Chlamydial Major Outer Membrane Protein Extract as a Trachoma Vaccine Candidate; Investigative Ophthalmology & Visual Science; 36(8): 1477-1491) (Year: 1995).*
Dumoux et al. 2013 (Penicillin kills chlamydia following the fusion of bacteria with Lysosomes and prevents Genital Inflammatory Lesions in C. muridarum-infected Mice; PLoS One 8(12):e83511) (Year: 2013).*
Mauro Campos, et al., "A Chlamydial Major Outer Membrane Protein Extract as a Trachoma Vaccine Candidate," Investigative Ophthalmology & Visual Science, Jul. 1995, vol. 36, No. 8, pp. 1477-1491.
Dumoux M, Le Gall SM, Habbeddine M, Delarbre C, Hayward RD, et al. (2013) Penicillin Kills Chlamydia following the Fusion of Bacteria with Lysosomes and Prevents Genital Inflammatory Lesions in C. muridarum-Infected Mice. PLoS One 8(12): e83511. doi:10.1371/journal.pone.0083511.
Victoria LM Herrera, et al., "Chlamydia pneumoniae Accelerates Coronary Artery Disease Progression in Transgenic Hyperlipidemia-Genetic Hypertension Rat Model," Molecular Medicine, May-Aug. 2003, vol. 9, No. 5-8, pp. 135-142.
Theresa D. Joseph, "A heat-labile protein of Chlamydia trachomatis binds to HeLa cells and inhibits the adherence of chlamydiae," Proc. Natl. Acad. Sci. USA vol. 88, pp. 4054-4058, May 1991.
G. W. Liechti, et al., "A new metabolic cell-wall labelling method reveals peptidoglycan in Chlamydia trachomatis," Nature vol. 506, 2014, pp. 507.
Hang Lu,, et al., "GM-CSF Transgene-Based Adjuvant Allows the Establishment of Protective Mucosal Inactivated Chlamydia trachomatis Immunity Following Vaccination with," J Immunol 2002; 169:6324-6331; doi: 10.4049/iimmunol.169.11.6324.

* cited by examiner

*Primary Examiner* — Mary Maille Lyons
(74) *Attorney, Agent, or Firm* — Arrigo, Lee, Gutman & Mouta-Bellum LLP

(57) ABSTRACT

The invention relates to vaccine compositions for treating and/or preventing infections by a bacterium of the Chlamydiaceae family, said compositions comprising bacteria of the Chlamydiaceae family, which have been previously treated by at least one peptidoglycan inhibitor, or extracts of said treated bacteria.

5 Claims, 18 Drawing Sheets

Number of CD4+T cells

A

Number of CD25+ CD4+T cells

B

Figure 1:
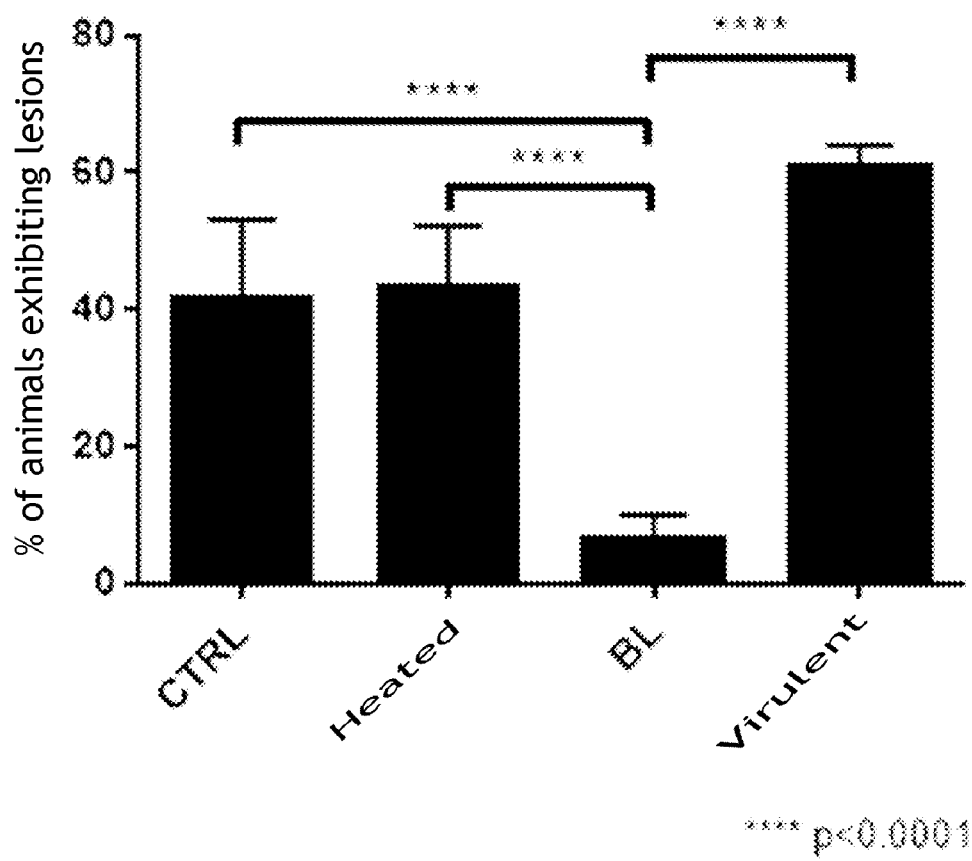

Number of CD44$^{hi}$ CD62L$^{low}$ CD4$^+$ T cells

C

Number of ICOS$^+$ CD4$^+$ T cells

D

Number of CD8+ T cells

A

Number of ICOS+ CD8+ T cells

B

I-Lymph nodes
(draining the genital tract)

II-Spleen

Spleen

Nombre de cellules T CD4⁺

A

Number of CD25⁺ CD4⁺ T cells

B

Number of CD44$^{hi}$ CD62L$^{low}$ CD4$^+$ T cells

C

Number of CD8$^+$ T cells

D

Number of CD25⁺ CD8⁺ T cells

E

Number of CD44$^{hi}$ CD62L$^{low}$ CD8⁺ T cells

F

Lymph nodes
(draining the genital tract)

Number of CD4⁺ T cells

A

Number of CD44$^{hi}$ CD62L$^{low}$ CD4⁺ T cells

B

Number of CD25+ CD4+ T cells

C

Number of ICOS^hi CD4+ T cells

D

Number of CD8⁺ T cells

E

Number of CD44$^{hi}$ CD62L$^{low}$ CD8⁺ T cells

F

I-Lymph nodes
(draining the genital tract)

II-Spleen

I-Lymph nodes
(draining the genital tract)

II-Spleen

VACCINE COMPOSITION AGAINST *CHLAMYDIACEAE* INFECTIONS

INTRODUCTION

Infections with bacteria of the family Chlamydiaceae, which can affect humans and animals, are responsible for a set of particularly serious pathologies.

*Chlamydia* infection is the most common sexually transmitted disease of bacterial origin with nearly 106 million new cases per year. Effective antibiotic treatments exist but this disease is often asymptomatic (75% of women and 50% of men). Most patients are thus not treated because they are not diagnosed, and the consequences of an untreated infection can be serious (sterility, ectopic pregnancies, premature births, neonatal infections).

Thus, the development of a vaccine is a major healthcare issue in order to eradicate the disease.

There exists to date no effective vaccine for preventing Chlamydiae infections in humans. Various vaccine strategies have been carried out during the past 20 years, but problems related to low immunogenicity (antigen vaccines, inactivated forms) or to regulatory issues (attenuated live forms that can be reactivated) have not allowed these vaccines to be tested in the clinical phase.

The family Chlamydiaceae comprises two genera, *Chlamydia* and *Chlamydophila*, each comprising several species; each species is composed of various biovars and serovars. Each of these species causes a set of disabling pathologies in humans and animals, and can even be deadly in the case of infections with *C. psittaci*.

Bacteria of the family Chlamydiaceae are Gram-negative. They are referred to as "obligate intracellular" bacteria because they can grow and multiply only in a parasitophorous vacuole within an infected eukaryotic cell. During development, bacteria of the family Chlamydiaceae take two forms:

- the elementary body (EB), which is the infectious form and does not divide, and
- the reticulate body (RB), which is noninfectious, obligate intracellular and which divides by binary fission.

The EB enters the host cell within a vesicle. If several EB infect the same cell, the vesicles generally assemble at the centrosome and fuse to form the inclusion. After 5 to 12 hours of infection, EB differentiate into RB, which actively multiply. After 30 to 40 hours, RB convert into EB; the inclusion and the host cell are then lysed, releasing the bacterial progeny to infect nearby cells. All these parameters can vary from one serovar and bacterial species to another, and according to the experimental conditions (Fields, K. A. & T. Hackstadt, *Annu Rev Cell Dev Biol* 18: 221-45, 2002).

During its development cycle, the bacterium deploys numerous strategies for surviving in the host cell. The *Chlamydia* bacterium notably inhibits host-cell apoptosis induced by external signals, inhibits fusion of lysosomes with the bacterial inclusion, diverts vesicular traffic toward the vacuole to enable the vacuole's growth, and injects into the cytoplasm multiple virulence factors, including a key protease (chlamydial protease/proteasome-like activity factor, CPAF) which induces the degradation of numerous eukaryotic proteins, including transcription factors for molecules of the major histocompatibility complex, which responsible for presenting antigens to the immune system cells.

To these mechanisms developed during a continuous bacterial cycle is added the phenomenon of persistence. In response to certain stresses in the cell environment, such as the presence of certain antibiotics or of interferon gamma (IFN-γ) or the absence of iron, the bacterium stops its bacterial cycle and its proliferative mechanism, thus becoming a persistent, viable body that cannot be cultured in vitro. Persistence explains a high level of interaction between the pathogen and the host and enables the bacterium to remain alive, or dormant ("persistent"), in the organism for months, even years. Indeed, although it is very difficult to demonstrate persistence in vivo, multiple studies suggest that a *Chlamydia* bacterium can exist for several years within tissues such as the genital tract, conjunctival mucosa and vascular tissue, thus causing recurrent infections and chronic inflammation (Beatty et al., *Microbiol Rev* 58(4): 686-99, 111994; Kern et al., *FEMS Immuno Med Microbiol.* 55(2): 131-9, 2009).

The high rate of asymptomatic infections and the severity of the pathologies justify the active search for a safe and effective vaccine for controlling *Chlamydia* infections. To date, roughly 40 vaccine tests have been carried out mainly in the mouse, using either inactivated bacteria or purified antigens or recombinant antigenic proteins, even DNA vaccines (see for example Hafner et al., *Vaccine,* 32(14): 1563-1571, 2014, Farris et al., *Infection and Immunity,* 79: 986-996, 2011, Schautteet et al., *Infect. Dis. Obstet. Gynecol.,* 2011: 963513, 2011; Campos et al., In vision and ophthalmology, 36(8) 1477-1491, WO 92/00096; Lu Hang et al., *The Journal of Immunology,* 169(11), 6324-6331). None have provided a convincing result. It is agreed that an attenuated form of the bacterium could be the basis for an excellent vaccine. Unfortunately, the Chlamydiaceae cannot be transformed and very few experimentally attenuated strains were able to be isolated.

Currently, there is no vaccine on the market for preventing Chlamydiaceae infections in humans. The asymptomatic nature of a large number of infections with bacteria of the family Chlamydiaceae and the severity of pathologies developed justify the search for a preventive vaccine which is safe and effective, i.e., which has a high immunogenicity while guaranteeing a low risk of infection for the subject.

The inventors found that, very surprisingly and contrary to existing biases, the Chlamydiaceae forms inactivated by a peptidoglycan inhibitor, in particular ß-lactams or D-cycloserine, can be used very effectively to manufacture medicinal products for the prophylactic treatment of infections with bacteria of the family Chlamydiaceae.

DESCRIPTION OF THE INVENTION

The inventors have previously shown that treating cell cultures infected with bacteria of the family Chlamydiaceae, with peptidoglycan inhibitors, notably with ß-lactams, leads to the formation of abnormal bacterial forms, the BL forms, which have lost all infectivity (WO 2011/086134; Dumoux et al., *PLoS One.* 8(12):e83511, 2013). These results were subsequently confirmed by other laboratories. (Ouellette et al., *Mol Microbiol.* 85(1): 164-178, 2012; Pilhofer et al., *Nat Commun.* 4:2856, 2013; Liechti et al., *Nature.* 506(7489): 507-510, 2014). The inventors have now found that, quite surprisingly, the BL forms always present native antigens, even when these forms are abnormally dilated and absolutely no longer infectious.

Injecting BL forms into mice thus makes it possible to protect these animals against subsequent infections with infectious bacteria. This BL form thus represents an inactivated form that can be used to immunize naive individuals likely to be infected with Chlamydiaceae.

The inventors showed that the BL form obtained by treating bacteria of the family Chlamydiaceae with a peptidoglycan inhibitor, notably with a ß-lactam, is immunogenic. The term "immunogenic" as intended herein refers to the capacity of a molecule to trigger an immune response, whether humoral, cell-mediated or both. An immune response to an immunogenic bacterial form, as understood herein, means the development in a subject of a humoral and/or cell-mediated immune response to one or more molecules present in said bacterial form (for example, an antigen, such as a protein, a glycolipid (LPS) or a polysaccharide). The expression "humoral immune response" means an immune reaction the effectors of which are soluble molecules, such as for example antibodies. These are notably produced by plasmocytes and lymphocytes. A "cell-mediated immune response" in the context of the invention is an immune reaction the effectors of which are cells such as cytotoxic T lymphocytes, killer T cells, or helper T cells. A "cell-mediated immune response" in the context of the invention also comprises the production of cytokines, chemokines and other similar molecules produced by activated T cells and/or other hematopoietic cells, including those derived from $CD4^+$ or $CD8^+$ T lymphocytes, and/or epithelial cells. The capacity of an antigen or of a particular bacterial form to stimulate a cell-mediated immune response can be easily determined by persons skilled in the art. There exists in the art a large number of tests for this purpose (see for example, Erickson et al., *J. Immunol.* 151: 4189-4199, 1993; Doe et al., *Eur. J. Immunol.* (24: 2369-2376, 1994).

In particular, the BL form of the present invention is capable of triggering an immune response of Chlamydiae-specific antibody-producing B lymphocytes and T lymphocytes (TL) in the spleen. In response to intravaginal infection with *Chlamydia*, these activated effector TL (effectors or regulators) are capable of leaving the spleen for the lymph nodes draining the genital tract, the site of infection.

According to a first aspect, the invention has as an object a vaccine composition comprising bacteria of the family Chlamydiaceae first treated with at least one peptidoglycan inhibitor, notably with a ß-lactam, or extracts thereof for use in the prophylactic and/or therapeutic treatment of infections with bacteria of the family Chlamydiaceae.

In the context of the invention, the term "family Chlamydiaceae" refers to the taxonomic unit composed of two genera, *Chlamydia* and *Chlamydophila*, as defined in Bush & Everett, *Int J Syst Evol Microbiol.* 51 (Pt 1): 203-20, 2001. Similarly, in the context of the invention, the term "genus *Chlamydia*" refers the taxonomic unit comprising the species *Chlamydia trachomatis, Chlamydia suis* and *Chlamydia muridarum*, and "genus *Chamydophila*" refers to the taxonomic unit composed of the species *Chlamydophila abortus, Chlamydophila psittaci, Chlamydophila caviae, Chlamydophila pecorum, Chlamydophila fells* and *Chlamydophila pneumoniae* (Bush & Everett, *Int J Syst Evol Microbiol.* (51 (Pt 1): 203-20, 2001). It is well-known to persons skilled in the art that these species have distinct host ranges: for example, *Chlamydia trachomatis* and *Chlamydophila pneumoniae* are responsible for infections in humans, *Chlamydia suis* in pigs and *Chlamydophila abortus* in ruminants. The invention is not limited to a specific bacterial species, but can be applied to any species of the family Chlamydiaceae and, in particular, to those mentioned above.

Various adjuvants are commonly used in the manufacture of vaccine compositions in order to thereby increase immunogenicity, for example by stimulating the immune system. In the context of the invention, the term "adjuvant" describes any substance added to accelerate, prolong, strengthen or modify the quality of the specific immune response induced by the composition according to the invention when the additive and the composition according to the invention are used together. The adjuvants are thus products that increase the reactions of the innate and adaptive immune system, when they are administered in the presence of antigens of viral, bacterial or synthetic origin. They cause the massive attraction of macrophages to the injection site, then in the lymph nodes; they activate dendritic cells; they increase the production of specific immunoglobulins, antibodies; and they stimulate numerous cells involved in the mechanisms of immune defense.

Thus, according to a particular embodiment, the composition according to the invention further comprises a pharmaceutically acceptable adjuvant. The pharmaceutically acceptable adjuvants are well-known to persons skilled in the art and may be selected as a function of the intrinsic and advantageous properties of these adjuvants, such as those described by Petrovsky et al., *Immunology and Cell Biology,* 82: 488-496, 2004 or Vermout et al., *Ann. Méd. Vét.* 147: 393-401, 2003. Furthermore, it is well-known that the immunologic adjuvants can be adapted in particular as a function of the route of administration selected.

The adjuvant according to the invention will be for example selected from bacterial components, bacterial toxins, oily adjuvants, mineral adjuvants, CpG oligodeoxynucleotides, saponins, vesicular or nanoparticular adjuvants, synthetic copolymers, lipophilic amines, cytokines, imidazoquinolones, or polysaccharides.

Among the bacterial components that can be used as adjuvants according to the invention, by way of example, mention may be made of:

- Bacillus Calmette-Guérin or BCG, which comprises a strain of attenuated *Mycobacterium bovis*
- Muramyl dipeptide (N-acetylmuramyl-l-alanyl-D-isoglutamine) or MPD, and the synthetic derivatives thereof
- Trehalose dimycolate or TMD
- The endotoxin of Gram-negative bacteria, also called lipolysaccharide or LPS and the derivative thereof monophosphoryl lipid A or MPL.

Among the bacterial toxins that can be used as adjuvants according to the invention, by way of illustration, mention may be made of:

- Cholera toxin from *Vibrio cholerae* (CT), in particular the purified sub-unit B thereof (CTB).
- Pertussis toxin from *Bordetella pertussis* (PT) in inactivated form
- Thermolabile lymphotoxin from *Escherichia coli* (TL)

Among the oily adjuvants that can be used as adjuvants according to the invention, by way of illustration, mention may be made of:

- The squalene-based oily adjuvants such as for example TiterMax (marketed under that name by Vaxcel Norcross Ga. USA) or RIBI adjuvant system (product marketed under that name by Ribi Immunochem Research, Hamilton, Mont. USA).

Among the mineral adjuvants that can be used as adjuvants according to the invention, by way of example, mention may be made of alum, the name commonly used to refer to the compounds aluminum hydroxide and aluminum phosphate, potassium phosphate or calcium phosphate.

Among the saponins that can be used as adjuvants according to the invention, by way of example, mention may be made of those extracted from the bark of *Quillaja saponaria molina* (Quit A), preferentially purified forms QS-21 and QS-7 (see for reference Kensil et al. *Dev Bio Stand.;* 92: 41-7. 1998).

Among the synthetic copolymers that can be used as adjuvants according to the invention, by way of example, mention may be made of synthetic amphipathic copolymers composed of hydrophilic chains of polyoxyethylene (POE) and hydrophobic chains of polyoxypropylene (POP) or dimethyldioctadecylammonium bromide or chloride (DDA).

Among the lipophilic amines that can be used as adjuvants according to the invention, by way of example, mention may be made of avridine.

Among the cytokines that can be used as adjuvants according to the invention, by way of example, mention may be made of histamine, interferon, in particular INFα, interleukins, in particular IL-1 and IL-2.

Among the imidazolquinolones that can be used as adjuvants according to the invention, by way of example, mention may be made of imiquimod or resiquimod.

Among the polysaccharides that can be used as adjuvants according to the invention, by way of example, mention may be made of dextrans, mannans, glucans, chitosans.

According to the invention, the adjuvant is also for example rubber, ASO3 (compound consisting of squalene, DL-α-tocopherol and polysorbate), MF59C.1 (compound consisting of polysorbate 80, squalene, sorbitan trioleate, sodium citrate, citric acid and water).

The inventors discovered that, surprisingly, bacteria of the family Chlamydiaceae treated with peptidoglycan inhibitors, notably with ß-lactams, as well as the fragments of these bacteria, are highly immunogenic. In fact, the vaccine compositions comprising these inactivated bacteria induce a very good protection in mice against vaginal infections with *Chlamydia muridarum*.

The inventors notably showed that the repeated administration of the vaccine compositions of the invention brings about a T lymphocyte immune response specific for *Chlamydia muridarum* in the spleen. In response to intravaginal infection with *Chlamydia muridarum*, these activated CD4+ and CD8+ TL and the regulatory T lymphocytes (CD4+ FoxP3+) leave the spleen for the lymph nodes draining the genital tract.

Herein, the term "T cells" or "T lymphocytes" refers a type of lymphocytes playing a central role in cell-mediated immunity. T lymphocytes can be distinguished from the other lymphocytes, such as B cells and natural killer (NK) cells, by the presence of a T lymphocyte receptor (TCR) on the cell surface. A "T cell receptor" or "TCR" as used herein is a receptor present on the surface of T cells responsible for the specific recognition of the antigens presented by the molecules of the major histocompatibility complex (MHC). CD4+ T lymphocytes, which express the CD4 glycoprotein on their surface, are distinguished from CD8+ T lymphocytes, characterized by the expression of the CD8 glycoprotein.

A "effector T lymphocyte" in the context of the invention is an T lymphocyte which provides a specialized function in the immune response, such as secreting cytokines or helping B lymphocytes in the humoral function (CD4+ T lymphocytes, also called auxiliary T lymphocytes) as well as a cytotoxic activity (CD8+ T lymphocytes). Surface markers which are overexpressed (ICOS, CD44) or underexpressed (CD62L) mark the activation state of effector T lymphocytes. "Regulatory lymphocytes" in the context of the invention are T cells which highly express the surface markers CD4 and CD25. These cells also express the marker FOXP3, which is a transcription factor (Battaglia and Rancarolo 2009). These regulatory lymphocytes are thus CD4+ CD25highFOXP3high. These cells are characterized by a capacity to suppress or negatively regulate immune reactions mediated by effector T cells, such as CD4+ or CD8+ effectors.

According to a second aspect, the present invention has as an object a process for preparing a vaccine composition for the prophylactic and/or therapeutic treatment of infections with bacteria of the family Chlamydiaceae, said process comprising a step of contacting, in vitro, bacteria, preferably intracellular bacteria of the family Chlamydiaceae, with at least one peptidoglycan inhibitor, notably at least one ß-lactam.

In the context of the invention, the term "peptidoglycan inhibitor" refers to any compound capable of inhibiting peptidoglycan synthesis or of affecting the structure thereof. The peptidoglycan inhibitors in the context of the invention comprise, among others, D-cycloserine (d-4-amino-3-isoxazolidinone), vancomycin, teicoplanin, bacitracin, daptomycin, ß-lactams. A "peptidoglycan inhibitor" in the context of the invention is preferably D-cycloserine or a ß-lactam.

Herein, the term "ß-lactam" refers to any antibiotic which contains a ß-lactam ring in its molecular structure. In the context of the invention, ß-lactams thus include penicillin derivatives as well as cephalosporines, monobactams, carbapenems, and ß-lactamase inhibitors. In particular, the ß-lactam according to the invention may be benzylpenicillin (penicillin G), phenoxymethylpenicillin (penicillin V), ampicillin (penicillin A), benzathine benzylpenicillin, meticillin, dicloxacillin, flucloxacillin, co-amoxiclav (amoxicillin+clavulanic acid), piperacillin, ticarcillin, azlocillin, carbenicillin, cephalexin, cefalotin, cefazolin, cefaclor, cefuroxime, cefamandole, cefotetan, cloxacillin, cefadroxil, cefixime, cefoxitin, ceftriaxone, cefotaxime, ceftazidime, cefepime, cefpirome, imipenem, imipenem in combination with cilastatin, cefixime in combination with imipenem, meropenem, mecillinam, ertapenem, aztreonam, clavulanic acid, tazobactam or sulbactam. In a preferred aspect of the invention, said ß-lactam is not amoxicillin. According to a more preferred embodiment of the invention, said ß-lactam is selected from the group consisting of benzylpenicillin (penicillin G), phenoxymethylpenicillin (penicillin V), cloxacillin, cefadroxil, cefixime, imipenem, cefixime in combination with imipenem, mecillinam, clavulanic acid, tazobactam and sulbactam. In an even more preferred embodiment, said ß-lactam is penicillin G. Persons skilled in the art will be able easily to determine the conditions for treating bacteria with the peptidoglycan inhibitors, particularly with ß-lactams, making it possible to obtain the BL forms used in the vaccine composition. The effect of ß-lactams on Chlamydiaceae phenotype in particular has been known since the 1970s. Generally, persons skilled in the art will be able to call upon the teaching of the publications of the inventors, as well as those of the other laboratories having shown an effect of ß-lactams on Chlamydiaceae (WO 2011/086134; Dumoux et al., *PLoS One.* 8(12):e83511, 2013; Ouellette et al., *Mol Microbiol.* 85(1): 164-178, 2012; Pilhofer et al., *Nat Commun.* 4:2856, 2013; Liechti et al., *Nature.* 506(7489): 507-510, 2014).

In particular, the concentration of peptidoglycan inhibitor, notably of ß lactam, to be used to obtain the BL forms may be easily evaluated based on the publications of the prior art, notably the publications of the inventors.

For example, a concentration of at least 100 µM, preferentially at least 200 µM, of D-cycloserine makes it possible to generate the BL forms.

According to a particular embodiment of the invention, the ß-lactam is used at a concentration greater than or equal to 0.1 µM, preferentially greater than or equal to 0.3 µM.

According to a first variant of the invention, cefadroxil or sulbactam is used at a concentration greater than or equal to 3 µM, preferentially greater than or equal to 10 µM. According to another variant of the invention, cefixime and imipenem are used in combination, each at a concentration greater than or equal to 30 µM. According to a particular aspect of the invention, cefixime or imipenem is used at a concentration greater than or equal to 100 µM, preferentially greater than or equal to 300 µM. According to a particular embodiment of the invention, mecillinam is used at a concentration greater than or equal to 1 µM, preferentially greater than or equal to 3 µM. According to another embodiment of the invention, tazobactam is used at a concentration greater than or equal to 10 µM, preferentially greater than or equal to 30 µM. According to a particular aspect of the invention, clavulanic acid is used at a concentration greater than or equal to 0.3 µM, preferentially greater than or equal to 1 µM. According to a particularly advantageous variant of the invention, amoxicillin, benzylpenicillin (penicillin G), phenoxymethylpenicillin (penicillin V), cloxacillin or mecillinam is used at a concentration greater than or equal to 0.1 µM, preferentially greater than or equal to 0.3 µM.

Similarly, persons skilled in the art will be able to determine the incubation period of the bacteria with the peptidoglycan inhibitors, notably the ß-lactams, necessary to produce the BL forms. They will be able for example to monitor the appearance of such forms with a microscope. As explained above, they will also be able to consult the publications of the prior art.

It is thus particularly advantageous to incubate the bacteria with said peptidoglycan inhibitors, including notably ß-lactams, during the time of complete development of the bacterial inclusion, i.e., until it fills 80% to 90% of the cell volume. According to a preferred embodiment of the invention, bacteria of the family Chlamydiaceae are contacted with said inhibitor for at least 1 hour, preferentially at least 2 hours, more preferentially at least 3 hours, even more preferentially at least 4 hours, still more preferentially at least 5 hours, in an even more preferred manner at least 10 hours, in yet an even more preferred manner at least 24 hours.

Bacteria of the family Chlamydiaceae exist in various forms, according to the phase of their life cycle. The virulent form of these bacteria is the elementary body. The latter is adapted to survival in the external environment, with no possibility of multiplication but with the ability to enter, likely by phagocytosis, into the host cell. In the vacuole, the elementary body is transformed into a reticulate body, a larger element whose DNA is decondensed and which can multiply to give elementary bodies which will then be released into the environment. The inventors showed that the bacteria are particularly sensitive to peptidoglycan inhibitors, notably to ß-lactams, after having infected eukaryotic cells. The aforesaid bacteria are then in the form of reticulate bodies which express the target enzymes of these inhibitors, which are essential to the biosynthesis of a molecule that regulates bacterial division. Advantageously, said bacteria of the invention are treated with said inhibitor, for example with a ß-lactam, after these bacteria have infected eukaryotic cells. In this case, it is advantageous in the vaccine composition to use a cell lysate of the infected eukaryotic cell, said lysate comprising said bacteria treated with the ß-lactam.

In this preferred embodiment, the present invention has as an object a process for preparing a composition for the prophylactic and/or therapeutic treatment of infections with bacteria of the family Chlamydiaceae, said process comprising the steps of:

a) contacting, in vitro, eukaryotic cells with bacteria of the family Chlamydiaceae, and obtaining infected eukaryotic cells;
b) incubating the infected eukaryotic cells obtained in step a) with at least one peptidoglycan inhibitor, notably at least one ß-lactam;
c) preparing a lysate of the cells of step b).

According to the invention, steps a) and b) of the process for preparing the vaccine composition are carried out under conventional cell culture conditions well-known to persons skilled in the art, who will be able to select and adapt them according to the type of eukaryotic cell used. Preferentially, steps a) and b) are carried out at a temperature of 37° C., a humidity level of 35%, and a $CO_2$ level of 5%. According to the invention, the cells are cultured in a suitable culture medium. According to an aspect of the invention, the incubation of step b) is maintained for at least 1 hour, preferentially at least 2 hours, more preferentially at least 3 hours, even more preferentially at least 4 hours, still more preferentially at least 5 hours, in an even more preferred manner at least 10 hours, in yet a still more preferred manner at least 24 hours.

The eukaryotic cells according to the invention are animal cells, preferentially mammalian cells or avian cells. The latter are for example cells of the order Galliformes, such as those of the chicken (*Gallus gallus*), or of the order Anseriformes, such as those of the mallard duck (*Anas platyrhynchos*) or of the Muscovy duck (*Cairina moschata*). The mammalian cells according to the invention are for example eukaryotic cells derived from rodents (Rodentiens), porcine eukaryotic cells (Suidae), or eukaryotic cells of primates. The eukaryotic cells of rodents are for example of the family of murids (Muridae), which include, among others, the subfamilies of hamsters (Cricetinae) or of mice and rats (Murinae), to which for example the mouse (*Mus musculus*) and the rat (*Rattus norvegicus*) belong. The porcine eukaryotic cells comprise, among others, the eukaryotic cells of the domestic pig (*Sus scrofa domesticus*). The eukaryotic cells of the order of primates comprise, among others, the eukaryotic cells of the family Cercopithecidae, in which may be mentioned for example the green monkey (*Chlorocebus sabaeus*), or of the family Hominidae, which comprises in particular humans (*Homo sapiens*). However, the eukaryotic cells in the context of the present invention do not comprise cells the obtaining of which requires or required the destruction of human embryos.

According to an embodiment of the invention, the eukaryotic cells are primary cells or immortalized or tumor cell lines, such as, for example, eukaryotic cells from cell lines. "Primary cells" are defined as being a group of original cells derived from normal tissue up to the $10^{th}$ passage inclusive, used for the production of biological products. In the context of the invention, the term "immortalized cells" refers to cells dividing beyond the Hayflick limit, cells which can be immortalized spontaneously or due to the implementation of an immortalization technique. Cell immortalization techniques are well-known to persons skilled in the art, who will be able to select from among them those most suited to their objective. By way of example, and without however limiting the invention to these examples, as an immortalization technique mention may be made of transformation by an oncogene, such as for example those encoding the SV40 T antigen, the Ras protein, the Myc protein or the Abl protein, or the overexpression of a reverse transcriptase of telomerase, for example hTERT, or the culture of eukaryotic cells to confluence during several passages. The eukaryotic cells used are selected for example from epithelial cells or fibroblats. Thus, according to an embodiment of the invention, the eukaryotic cells used are, by way of example, primary fibroblasts of embryonic origin, such as for example chick embryo fibroblasts (CEF), rat embryo fibroblasts (REF) or mouse embryo fibroblasts (MEF). It is also possible to use avian stem cell lines, as described in WO 2008/129058). Preferentially, the eukaryotic cells according to the invention come from cell lines. According to an advantageous embodiment, the eukaryotic cells according to the invention come from one of the lines selected from the immortalized cell lines NIH3T3, Vero, COS-7, the tumor lines Caco-2, CHO, PC12, HeLa, Jurkat, HL-60, the lines AtT20, GH3, HEK-293, HT29, HT-29, LNCap, MCF-7, MDA-MB-231, MDCK, Saos-2, Sf9, Sf21, S2, T-47D, U2OS and EB66® (Valneva, France). These cells are commonly used by the laboratories working in the field. They are available from cell culture collections such as the ATCC (American Type Culture Collection) or the DSMZ (Deutsche Sammlung von Mikroorganismen and Zellkulturen), or commercially. Persons skilled in the art will be able to select as needed the eukaryotic cells according to the invention as a function of the bacterium used or indeed as a function of the subject for which the composition according to the invention is intended.

Whole bacteria can be used as immunogen in the vaccine composition of the invention, once they have been treated with said peptidoglycan inhibitor, notably a ß-lactam. However, persons skilled in the art will easily understand that extracts of the bacteria thus treated can also be used in said vaccine composition, in so far as said extracts present intact native antigens. According to a first embodiment, said extract is a membrane extract. According to another embodiment, the extract is a cytoplasmic extract.

Protocols for isolating membrane extracts have been described in the art (see for example Frohlich et al., *J Microbiol Methods.* 91(2): 222-230, 2012) and can be used to obtain such extracts. They notably comprise two steps, a first of nitrogen cavitation and a second of immunoprecipitation with antibodies against the LPS of bacteria of the family Chlamydiaceae.

Nitrogen cavitation makes it possible to lyse eukaryotic cells gently, with no sudden temperature increase in the sample (Gottlieb & Adachi, Methods Enzymol. 322: 213-221, 2000). Advantageously, certain types of eukaryotic cell debris are removed by low-speed centrifugation (between 3 000 $g$ and 6000 $g$), while the bacteria remain in the supernatant. In a preferred embodiment, the method of the invention will thus comprise an additional step of low-speed centrifugation between the step of nitrogen cavitation and the step of immunoprecipitation with antibodies against the LPS of bacteria of the family Chlamydiaceae. Gentle sonication in ice can also be used.

Antibodies against the LPS (or anti-MOMP, anti-InC, anti-PMP or anti-CPAF antibodies, etc.) of the family Chlamydiaceae have been described in the prior art (Herrera et al., *Mol. Med.* 9: 135-142, 2003). They make it possible to selectively isolate the bacterial membrane fraction in the immunoprecipitation step after having lysed the eukaryotic cells, while the bacterial cytoplasmic fraction remains in the supernatant.

It may be advantageous to enrich the bacterial fraction by subjecting the lysates cleared of cell debris to centrifugation in order to separate the bacterial membrane fraction remaining in the supernatant from the particulate fraction which precipitates. Preferably, the lysates are centrifuged at a speed ranging between 10,000 and 20,000 $g$, more preferably between 12,000 $g$ and 18,000 $g$, even more preferably between 14,000 $g$ and 17,000 $g$, and most preferably between 15,000 $g$ and 16,000 $g$. The cytoplasmic extracts may be obtained by subjecting the pellet to isopycnic ultracentrifugation, according to the conditions described by Frohlich et al. (*J Microbiol Methods.* 91(2): 222-230, 2012).

As shown by the inventors' results, the vaccine compositions of the invention are in particular useful for preventing or treating infections with bacteria of the family Chlamydiaceae, as well as the pathologies caused by said infections. The vaccine compositions of the invention are notably capable of triggering a specific immune reaction against bacteria of the family Chlamydiaceae. This reaction is characterized notably by a T lymphocyte immune response specific for *Chlamydia muridarum* in the spleen. In response to intravaginal infection with *Chlamydia muridarum*, these activated CD4+ and CD8+ TL and the regulatory T lymphocytes leave the spleen for the lymph nodes draining the genital tract. As shown by the results reported in the examples (see in particular examples 3 and 4), this immune response is capable of protecting the individual against bacteria of the family Chlamydiaceae. According to a third aspect, the invention thus also has as an object bacteria of the family Chlamydiaceae and/or extracts thereof characterized in that said bacteria have been first treated with at least one peptidoglycan inhibitor, notably at least one ß-lactam, for use in the prophylactic or therapeutic treatment of infections with bacteria of the family Chlamydiaceae.

The invention also has as an object the use of a composition comprising bacteria of the family Chlamydiaceae and/or extracts thereof characterized in that said bacteria have been first treated with a peptidoglycan inhibitor, notably at least one ß-lactam, to manufacture a medicinal product for the prophylactic or therapeutic treatment of infections with bacteria of the family Chlamydiaceae. Similarly, the invention also relates to a method of preferentially prophylactic treatment of infections with bacteria of the family Chlamydiaceae with a composition comprising bacteria of the family Chlamydiaceae and/or extracts thereof, said bacteria having been first treated with a peptidoglycan inhibitor, in particular at least at least one ß-lactam. According to a particular embodiment, said treatment method comprises a step of administering said composition to a subject at risk of being infected with bacteria. Preferentially, this administration causes an increase in the population of activated specific effector CD4+ and CD8+ T lymphocytes in the spleen then the migration thereof toward the lymph nodes draining the infected genital tract. Alternatively, according to another preferred embodiment, this administration causes a reduction in the population of regulatory T lymphocytes in the spleen and an increase in the lymph nodes draining the infected genital tract. More preferably, this administration causes an increase in the population of activated specific effector CD4+ and CD8+ T lymphocytes then their migration toward the lymph nodes draining the genital tract and a reduction in the population of regulatory T lymphocytes in the spleen and an increase in the lymph nodes draining the infected genital tract.

The expression "infection with a bacterium of the family Chlamydiaceae" or "infection with a Chlamydiaceae" refers to the presence in at least one cell of the patient's or the animal's body of said bacterium of the family Chlamydiaceae. The infection may be genital, ocular, respiratory or pulmonary; it may also affect other sites, such as the vascular endothelium or the joints.

Although a large number of infections caused by bacteria of the family Chlamydiaceae are asymptomatic, said infections may nevertheless cause serious pathologies in patients or animals. In the context of the invention, the expression "pathology caused by an infection with bacteria of the family Chlamydiaceae" refers to any pathology the triggering of which is directly or indirectly caused by an infection with at least one bacterium of the family Chlamydiaceae.

The pathologies caused by an infection with bacteria of the family Chlamydiaceae thus include, in the context of the invention, the pathologies caused by *Chlamydia suis, Chlamydia muridarum, abortus, Chlamydophila psittaci, Chlamydophila caviae, Chlamydophila pecorum* and *Chlamydophila fells*. In the context of the invention, said pathologies caused by an infection with Chlamydiaceae more particularly include abortions and neonatal deaths caused by *Chlamydophila abortus*, as well as conjunctivitis, keratoconjunctivitis, purulent rhinitis, enteritis, bronchopneumonia and pneumonia, caused in particular in pigs by *Chlamydia suis*.

In humans, these pathologies can in particular be genital pathologies or ocular pathologies or trachoma inducing blindness (*Chlamydia trachomatis*), but they may also be respiratory pathologies (neonatal pneumopathy). Thus, it is known that *Chlamydophila pneumoniae* infections cause a form of pneumonia and that *Chlamydophila psittaci* is responsible for psittacosis. It is also known that infections with bacteria of the family Chlamydiaceae spread within the organism causing a number of atypical infections and pathologies such as cardiovascular and circulatory dysfunctions (atheroma). Among the cardiovascular and circulatory dysfunctions caused by bacteria of the family Chlamydiaceae, mention may be made of valvular stenosis and atheroma, respectively. In addition, said bacteria of the family Chlamydiaceae can also cause inflammatory diseases and joint diseases. It is known in particular that these bacteria can cause severe arthritis.

However, in a preferred embodiment of the invention, the pathologies caused by an infection with bacteria of the family Chlamydiaceae are ocular pathologies or genital pathologies. According to a more particularly preferred aspect of the invention, the ocular pathologies caused by an infection with bacteria of the family Chlamydiaceae comprise trachoma. According to another more particularly preferred aspect, the genital pathologies caused by an infection with bacteria of the family Chlamydiaceae comprise venereal lymphogranuloma or Durand-Nicolas-Favre disease. According to still another more particularly preferred aspect of the invention, the human genital pathologies caused by an infection with bacteria of the family Chlamydiaceae comprise pathologies such as urethritis and orchiepididymitis. These can lead to a decrease in male fertility. According to still another more particularly preferred aspect of the invention, an infection with bacteria of the family Chlamydiaceae causes in women genital pathologies such as cervicovaginitis, cervicitis, endocervicitis, urethritis, endometritis or perihepatitis, which can give rise to complications such as upper genital tract infections and, in particular, salpingitis, which is capable of developing into, among other things, formation of pyosalpinx and hydrosalpinx, which totally obstruct the fallopian tubes. Salpingitis is thus the primary risk factor for tubal sterility and ectopic pregnancy in women.

It is well-known to persons skilled in the art that the incidence of infection is generally inversely correlated with the patient's state of health, and that the risk of infection is thus greater in individuals already infected with other microorganisms. The compositions further comprising other active ingredients, or a mixture of active ingredients, thus provide better protection of the subjects' general health, and consequently better protection against infections with bacteria of the family Chlamydiaceae.

Thus, according to a particularly advantageous variant of the invention, the composition further comprises another active ingredient. By way of example, this other active ingredient is, in the context of the invention, another vaccine composition.

Among the other vaccine compositions according to the invention, particular mention may be made of the vaccine compositions likely to decrease the risk of pneumococci infections, tetanus, poliomyelitis, influenza, diphtheria, whooping-cough, hepatitis B, hepatitis A, human papillomavirus (HPV), tuberculosis (for example by bacillus Calmette-Guérin). More preferably, said another vaccine composition is capable of increasing, in vaccinated individuals, the amplitude and the speed of the protective immune response.

Furthermore, persons skilled in the art will be able to best select the routes and modes of administration of the composition according to the invention, as well as the optimal dosing schedules and pharmaceutical forms, according to the criteria generally taken into account in the manufacture of a medicinal product or the establishment of a pharmaceutical or veterinary treatment. Preferably, these compounds will be administered via the systemic route, in particular via the intravenous route, via the intramuscular, intradermal, intraperitoneal or subcutaneous route, via the oral route, or via the topical route (by means of gel, aerosols, drops, etc.). it will be particularly advantageous according to the invention to administer the composition via the enteral, oral, parenteral (for example subcutaneous, intradermal or intramuscular) or mucosal route (for example intranasal, sublingual, intravaginal, transcutaneous). More preferably, the pharmaceutical composition of the invention will be administered in several doses, spread out over time. The mode of administration, dosing schedule and optimal pharmaceutical form thereof may be determined according to the criteria generally taken into account in establishing a treatment adapted to a patient such as for example the patient's age or body weight, the gravity of the patient's general state, tolerance to the treatment and the side effects observed.

The composition according to the invention is prepared in any pharmaceutical form known to persons skilled in the art, for example in liquid or gel form, such as solutions, suspensions, syrups, or in spray form, or in solid form, such as in the form of tablets, microspheres or capsules.

Advantageously, the composition according to the invention is prepared in solution or injectable suspension form. According to a variant of the invention, the composition is lyophilized in order to be provided or prepared in solid form.

The solution according to the invention is administered at a therapeutically effective dose, in particular at an immunogenic dose, i.e., capable of inducing an antigen-specific immune response. The antigen-specific immune response may be measured according to any technique known to persons skilled in the art. By way of example, the antigen-specific immune response is evaluated by measuring the concentration of antibodies (immunoglobulins or Ig) specific for the bacterium of the family Chlamydiaceae used, in the subject, in particular IgM, IgG and IgA, at a given time after the last administration of the composition, by an Elisa or Elispot test. The antigen-specific immune response is evaluated in biological samples from the subject, such as for example blood, serum, tears or vaginal secretions.

Persons skilled in the art will be able to adapt the dose of the composition according to the invention as a function of the route of administration chosen, the vaccination schedule, and the subject's characteristics, such as species, age, weight, general state of health. According to an embodiment, the composition according to the invention is administered according to a vaccination schedule comprising several administrations. For example, according to an embodiment, the composition is administered in a repeated manner between 2 and 4 times over a period of 15 to 90 days, then one or more booster administrations are carried out between 1 and 10 years after the first administration.

Depending on the pharmaceutical form and on the type of administration desired, the composition according to the invention further comprises at least one pharmaceutically acceptable excipient. By way of example, the composition according to the invention may further comprise diluents, such as sodium, calcium carbonate or lactose, for example, lubricating agents, such as for example magnesium stearate, dyes, flavor enhancers, texturing agents, antibiotics, for instance thimerosal or antibiotics of the ß-lactam family, proteins, notably albumin or ovalbumin, stabilizers, such as monosodium glutamate (MSG) and 2-phenoxyethanol.

According to a fourth aspect, the invention also has as an object a method of in vitro diagnosis of infection with a bacterium of the family Chlamydiaceae in a subject, comprising the steps consisting of:
a) contacting a sample from said subject with a bacterium of the family Chlamydiaceae first treated with at least one peptidoglycan inhibitor, notably a ß-lactam, and
b) determining the presence of antibodies in said sample which are capable of binding to said bacterium.

Such methods are well-known to persons skilled in the art and can be carried out using a large number of standard procedures, such as the detection of radioactivity, of fluorescence, of luminescence, of chemiluminescence, of absorbance, or by microscopy, imaging, etc. Thus, according to a preferred embodiment of the invention, said method comprises the steps consisting of:
a) contacting said sample with antibodies specific for said bacterium generated against said bacterium first treated with a peptidoglycan inhibitor, notably a ß-lactam, said antibodies comprising a label producing a detectable signal, or being fixed to a reagent labeled in a detectable manner;
b) allowing the bacterium present in said sample to bind thereto so as to form antigen/antibody complexes; and
c) determining the presence of said bacterium in said sample by means of said detectable label.

According to a fifth aspect, the invention relates to a diagnostic kit for detecting infection with a bacterium of the family Chlamydiaceae, comprising said bacterium first treated with a peptidoglycan inhibitor, notably a ß-lactam, together with substances for performing an analysis to determine humoral immunity against said bacterium, in a unit packaging container.

The diagnostic kits according to the invention include, without limitation, kits for immunological methods such as immunohistochemistry, enzyme-linked immunosorbent assay (ELISA), western blotting, immunoenzymometric assay, immunofluorometric assay, immunoluminometric assay, immunoradiometric assay (IRMA), enzyme-multiplied immunoassay technique (EMIT), lateral-flow immunoassay, dipstick tests, immuno-histo/cyto-chemistry and all other tests known to persons skilled in the art. These immunological methods make it possible to determine the presence or the absence of an antibody in a sample. They also make it possible to measure the amount of said antibody in the sample.

The invention thus also has as an object, according to a sixth aspect, the use of a bacterium of the family Chlamydiaceae first treated with a peptidoglycan inhibitor, notably a ß-lactam, as in vitro diagnostic reagent in a binding assay, optionally in a diagnostic kit, for detecting neutralizing antibody conferring immunity against said bacterium.

It also has as an object the use of antibodies specific for a bacterium of the family Chlamydiaceae generated against said bacterium first treated with a peptidoglycan inhibitor, notably a ß-lactam, as in vitro diagnostic reagent in a binding assay, optionally in a diagnostic kit, for detecting said bacterium.

In addition to the foregoing provisions, the present invention also comprises other features and advantages which will arise from the following examples, and which should be regarded as illustrating the invention without limiting the scope thereof.

FIGURE CAPTIONS

FIG. 1: Vaccine efficacy of the BL forms. The BL forms lead to a significant decrease in the number of infected mice.

Figure 2:
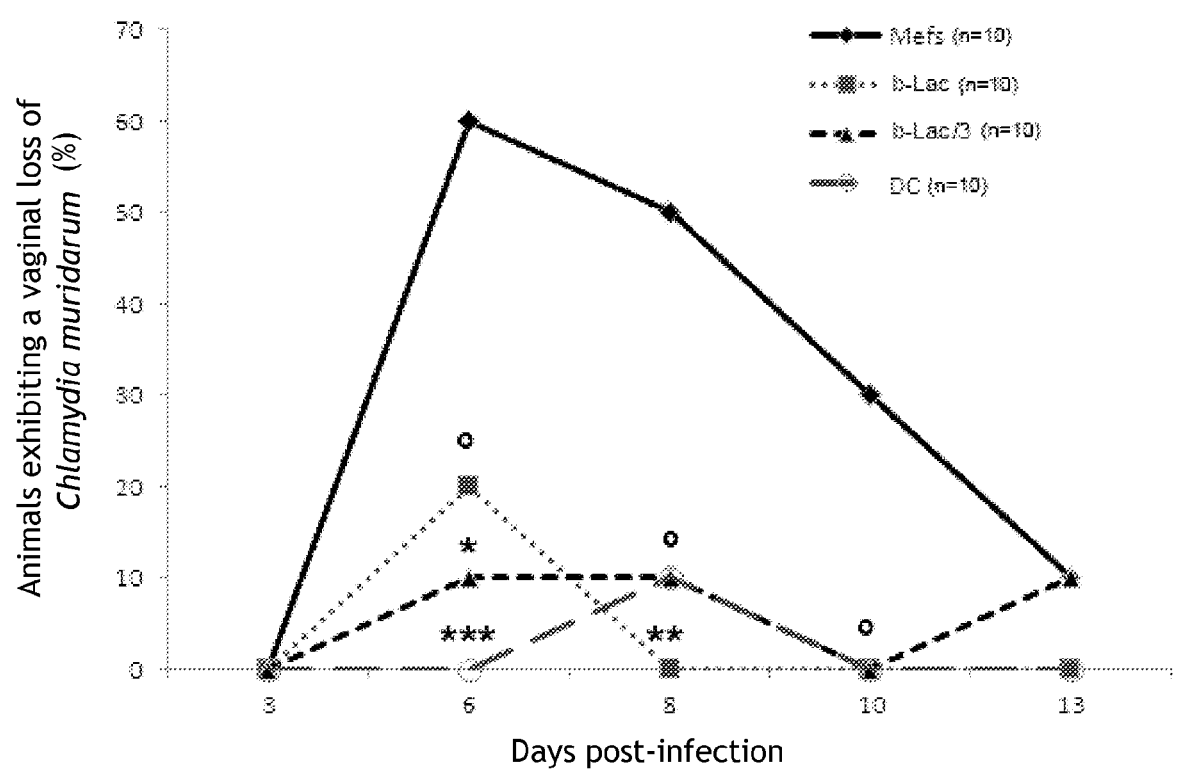
Figure 3:
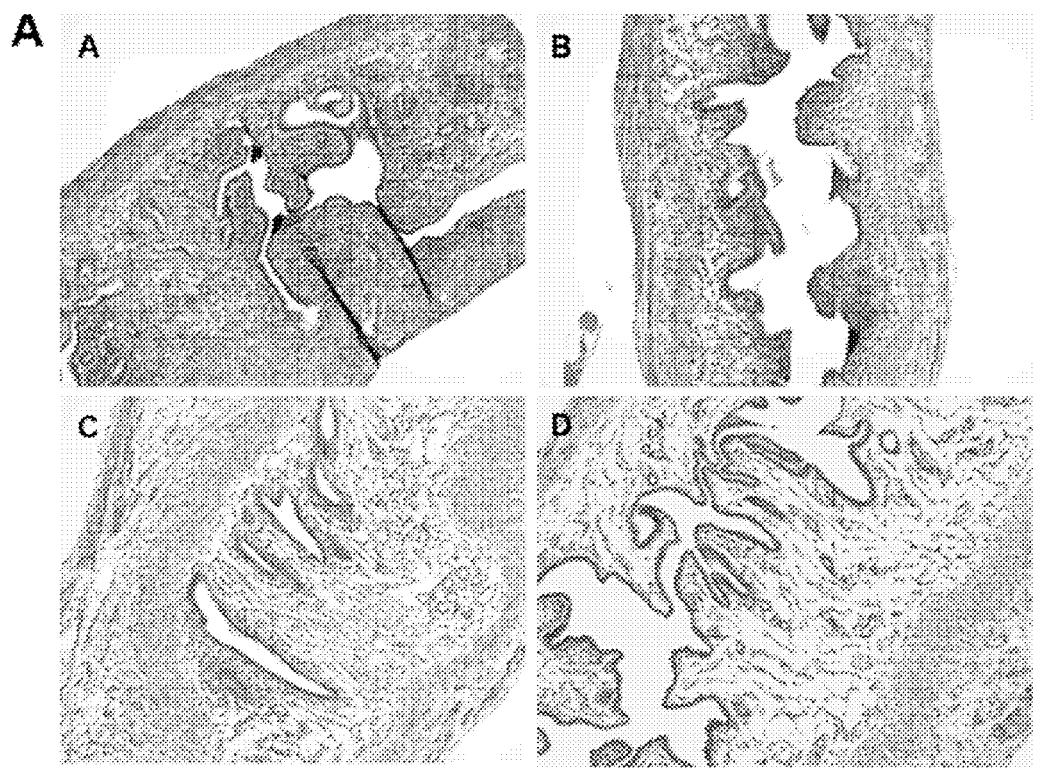
Figure 3:
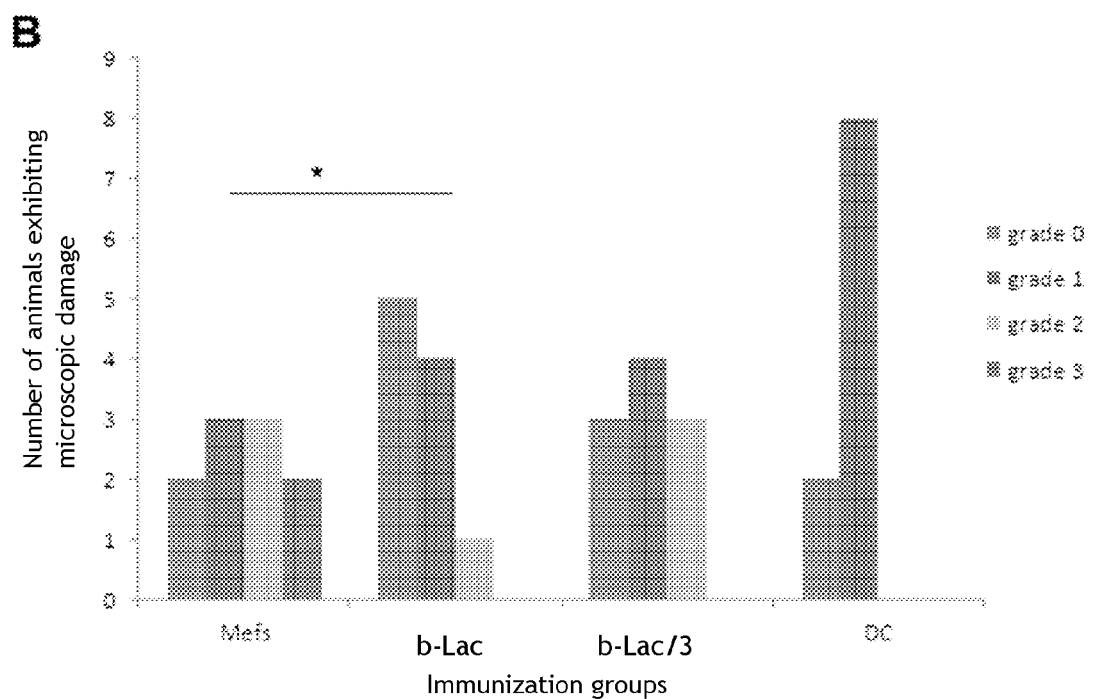
Figure 4:
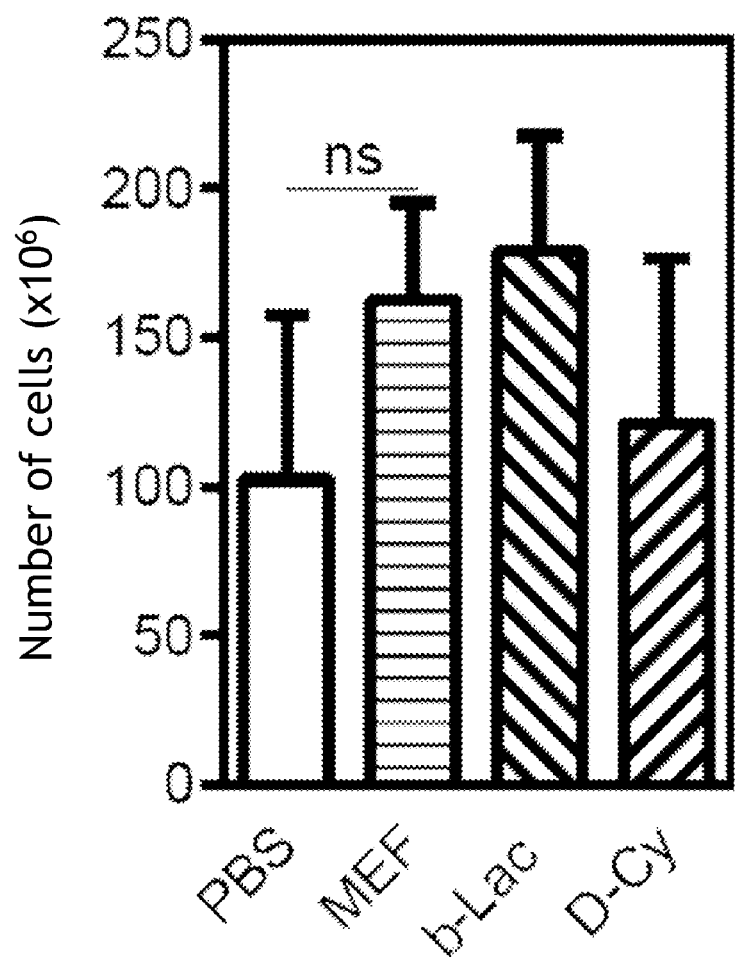
Figure 5:
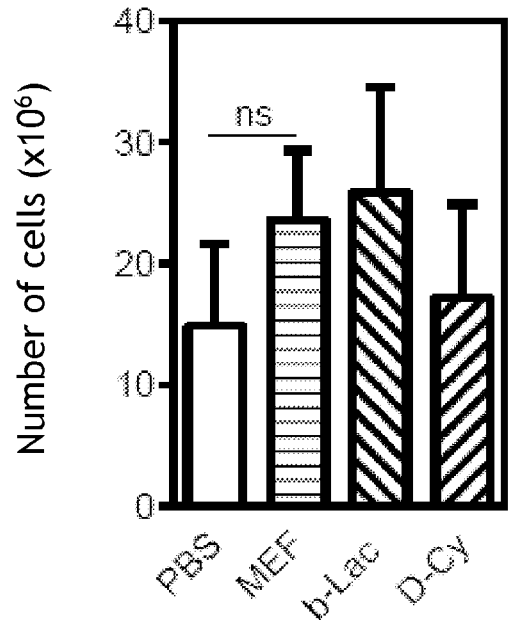
Figure 5:
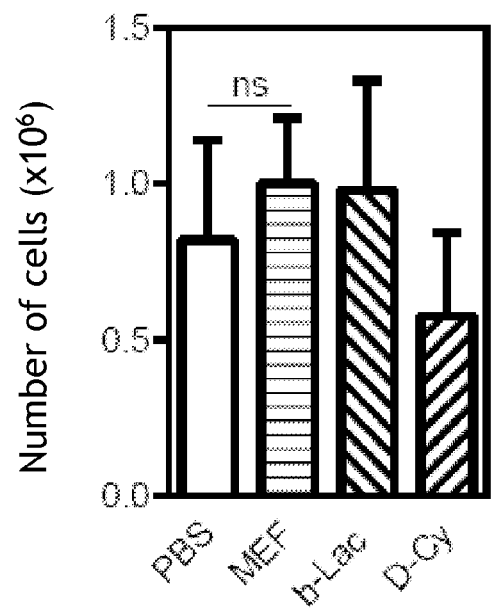
Figure 5:
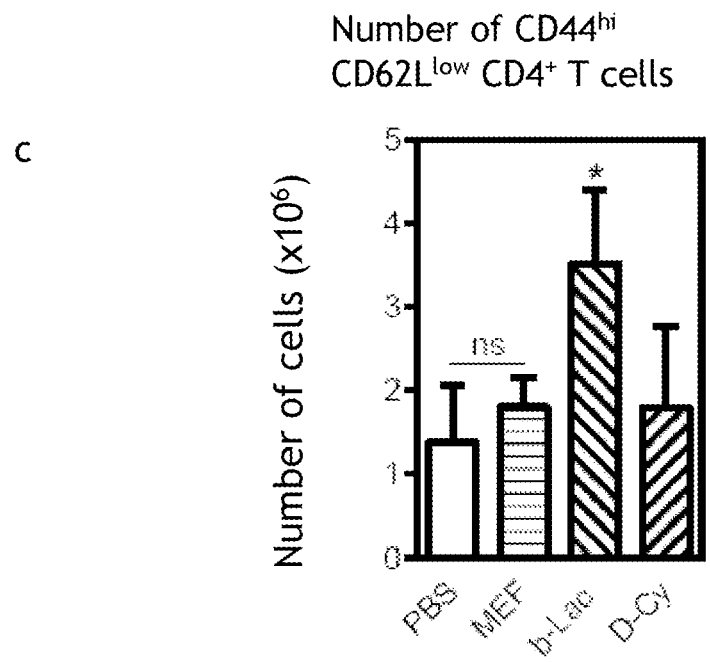
Figure 5:
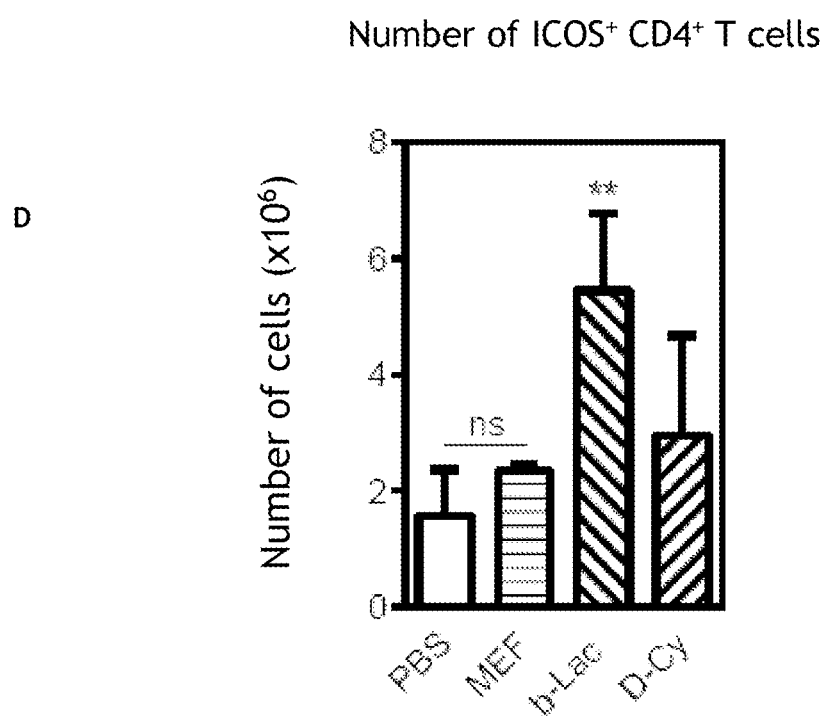
Figure 5:
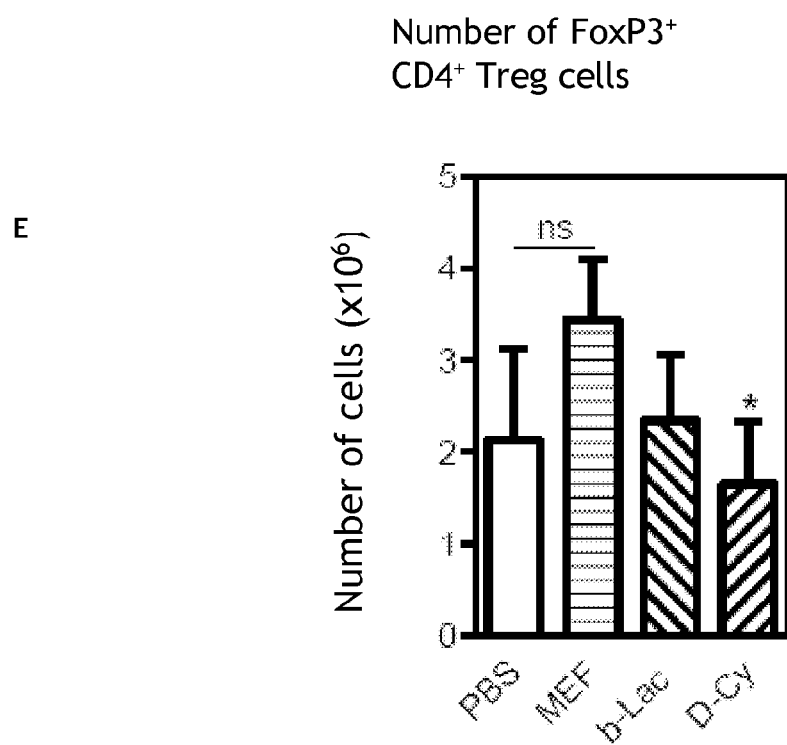
Figure 6:
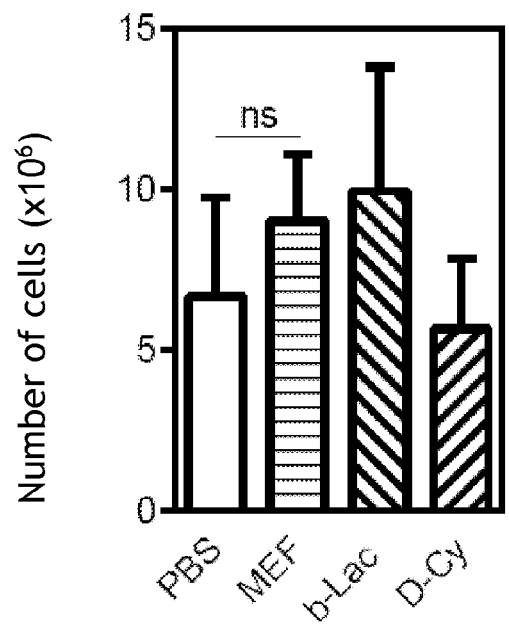
Figure 6:
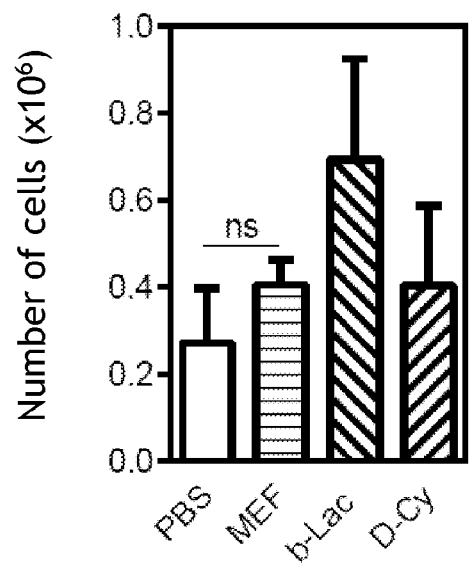
Figure 6:
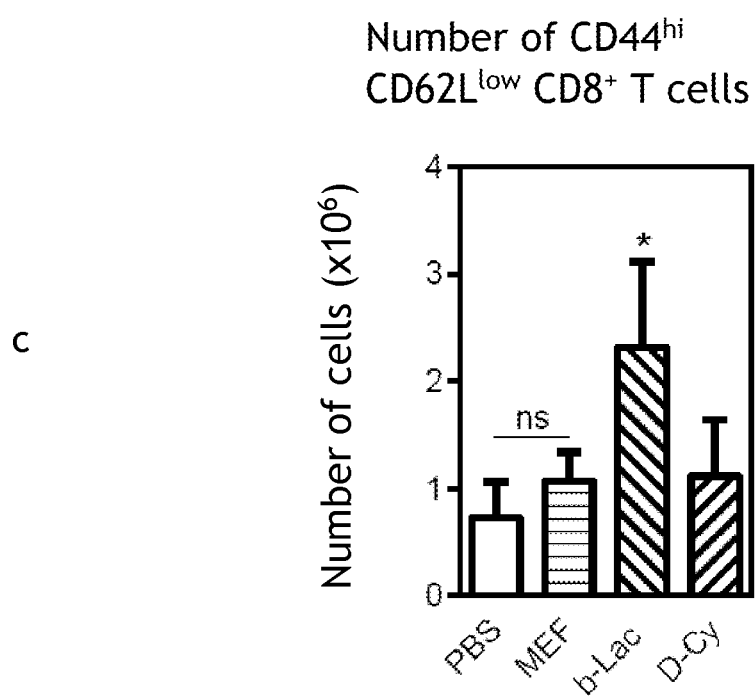

FIG. 2: Proportion of animals from the various immunization groups (Mefs, b-Lac, b-Lac/3, Dc) with a vaginal loss of *Chlamydia muridarum* at various times post-infection. °: $p<0.08$; *$p<0.05$; $p<0.01$; *$p<0.005$ relative to the Mefs group (Mann-Whitney test).

FIG. 3: A-Characterization of cell loss in the lamina propria of the uterine horns of mice, normal uterine horn grade 0, (A), grade 1 (B), grade 2 (C), grade 3 (D), photographs taken at 10× magnification. B-Evaluation of the severity of the microscopic damage of the uterine horns of animals from the various groups. Normal uterine horn (grade 0, A), grade 1 (B), grade 2 (C), grade 3 (D). *$p=0.054$ (Mann-Whitney test).

FIG. 4: Total number of splenic lymphocytes of mice after complete immunization with the vaccine or control forms. Isolated cells were counted in a Malassez cell and their number was calculated in relation to the number of viable cells analyzed by flow cytometry using a viability label (Fixable Viability Dye, BD Biosciences). Graph representative of an experiment on groups of animals tested individually (PBS, n=3; MEF, n=4; b-Lac, n=5; Dc, n=5). Means±SEM. The symbol "ns" or the absence of stars indicates the absence of statistically significant differences between the group of control animals immunized with sonicate of uninfected MEF cells and the group of control animals injected with PBS alone, or between MEF and b-Lac, or MEF and Dc groups.

FIG. 5: Total number of $CD4^+$ T lymphocytes and number activated after complete immunization with the vaccine forms. The total number of $CD4^+$ T lymphocytes (A) and the number of CD4+ T lymphocytes having activation markers are represented with a focus on membrane expression of CD25 (B), $CD44^{hi}$ $CD62L^{low}$ (C), $ICOS^+$ (D) and on intracellular expression of FoxP3 in order to show the population of regulatory T lymphocytes (E). Graphs representative of an experiment on groups of animals tested individually (PBS, n=3; MEF, n=4; b-Lac, n=5; Dc, n=5). Means±SEM. Unpaired t-test: the symbols *, **, represent measurements of p-values derived from tests carried out with respect to the control MEF (*$p\leq0.05$, **$p\leq0.01$). The symbol "ns" or the absence of stars indicates the absence of statistically significant differences between the group of control animals immunized with sonicate of uninfected MEF cells and the group of control animals injected with PBS alone, or between MEF and b-Lac, or MEF and Dc groups.

FIG. 6: Total number of CD8+ lymphocytes and number activated after complete immunization with the vaccine forms. The total number of CD8+ T lymphocytes (A) and the number of CD8+ T lymphocytes having activation markers are represented with a focus on membrane expression of ICOS (B) and of CD44$^{hi}$ CD62L$^{low}$ (C). Graphs representative of an experiment on groups of animals tested individually (PBS, n=3; MEF, n=4; b-Lac, n=5; Dc, n=5). Means±SEM. Unpaired t-test: the symbols *, represent measurements of p-values derived from tests carried out with respect to the control MEF (*p≤0.05). The symbol "ns" or the absence of stars indicates the absence of statistically significant differences between the group of control animals immunized with sonicate of uninfected MEF cells and the group of control animals injected with PBS alone, or between MEF and b-Lac, or MEF and Dc groups.

Figure 7:
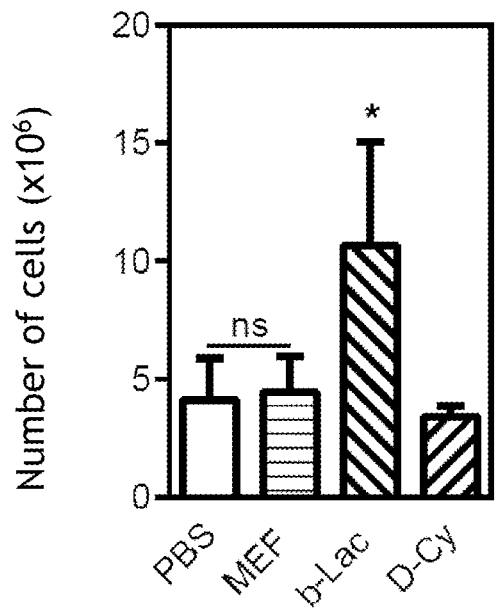
Figure 7:
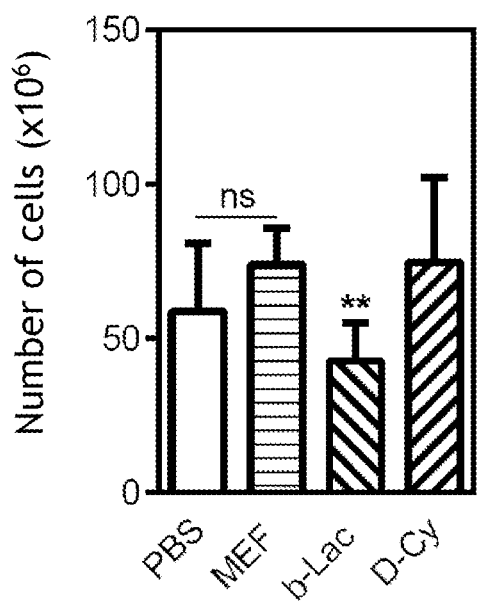

FIG. 7: Total number of cells in the lymph nodes and the spleen of mice after complete immunization with the vaccine forms, and one-week post-intravaginal infection with *Chlamydia muridarum*. Isolated cells were counted in a Malassez cell and their number was calculated in relation to the number of viable cells analyzed by flow cytometry using a viability label (Fixable Viability Dye, BD Biosciences). Graphs representative of an experiment on groups of animals tested individually (PBS, n=3; MEF, n=4; b-Lac, n=5; Dc, n=5). Means±SEM. Unpaired t-test: the symbols *, **, represent measurements of p-values derived from tests carried out with respect to the control MEF (*p≤0.05, **p≤0.01). The symbol "ns" or the absence of stars indicates the absence of statistically significant differences between the group of control animals immunized with sonicate of uninfected MEF cells and the group of control animals injected with PBS alone, or between MEF and b-Lac, or MEF and Dc groups.

Figure 8:
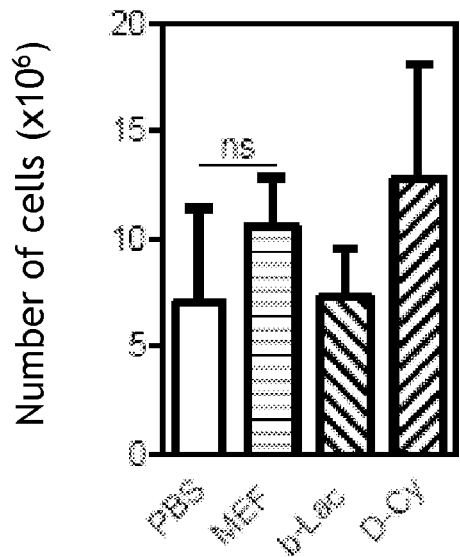
Figure 8:
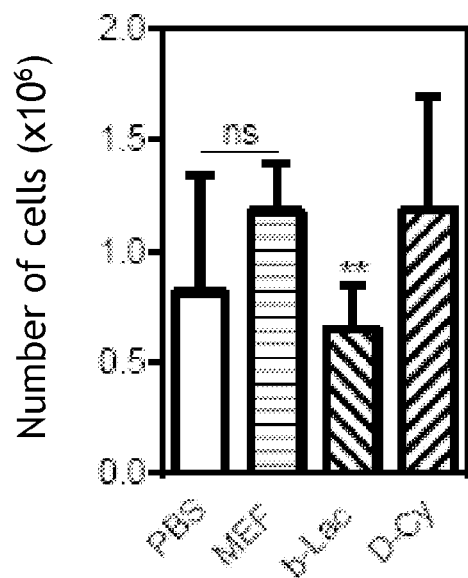
Figure 8:
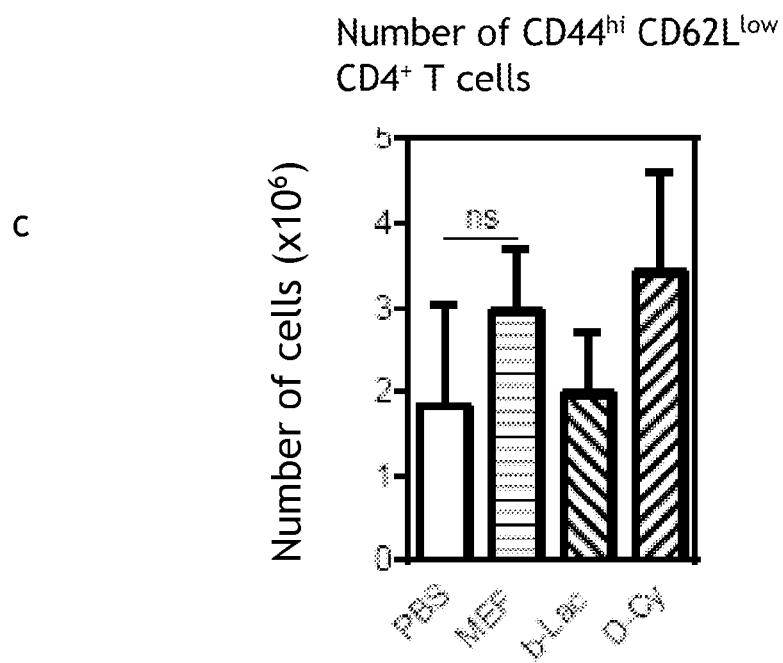
Figure 8:
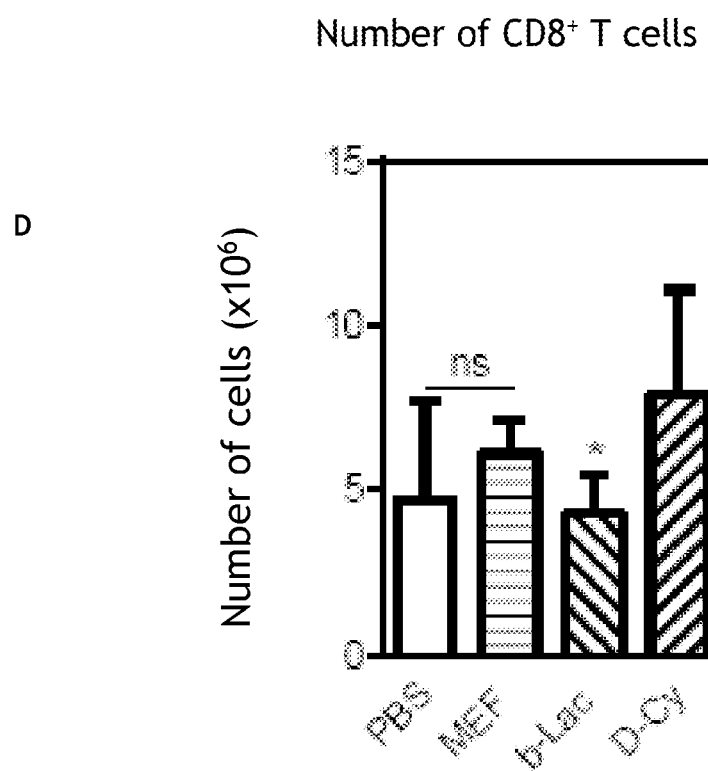
Figure 8:
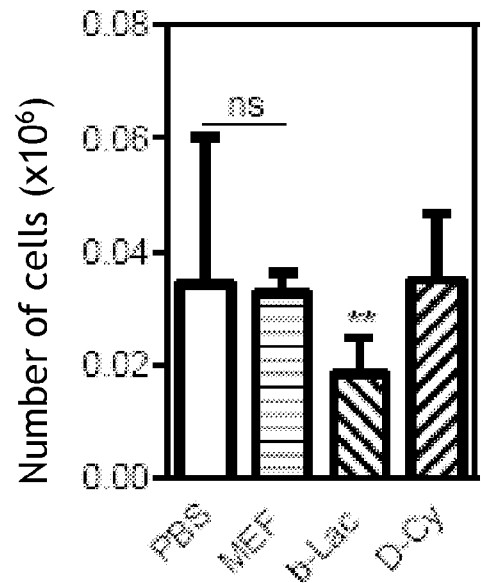
Figure 8:
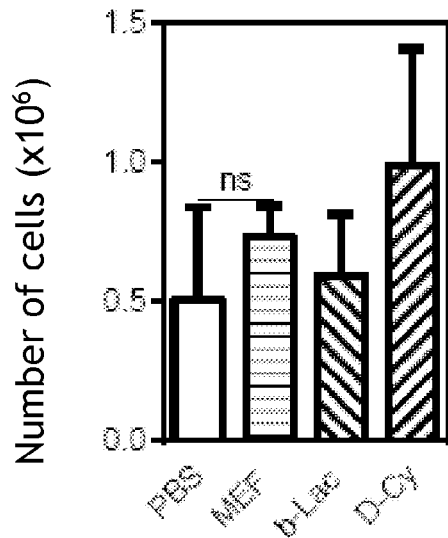

FIG. 8: Total number of splenic CD4+ T and CD8+ T lymphocytes and number activated after complete immunization with the vaccine forms and one-week post-intravaginal infection with *Chlamydia muridarum*. The total number of CD4+ (A) and CD8+ (D) T lymphocytes and the activation profile thereof are represented here with a focus on the number of CD25+ T lymphocytes among the CD4+ T (B) and CD8+ T (E), and on the number of CD44$^{hi}$ CD62L$^{low}$ CD4+ T and CD8+ T lymphocytes (C and F, respectively). Graphs representative of an experiment on groups of animals tested individually (PBS, n=3; MEF, n=4; b-Lac, n=5; Dc, n=5). Means±SEM. Unpaired t-test: the symbols *, **, represent measurements of p-values derived from tests carried out with respect to the control MEF (*p≤0.05, **p≤0.01). The symbol "ns" or the absence of stars indicates the absence of statistically significant differences between the group of control animals immunized with sonicate of uninfected MEF cells and the group of control animals injected with PBS alone, or between MEF and b-Lac, or MEF and Dc groups.

Figure 9:
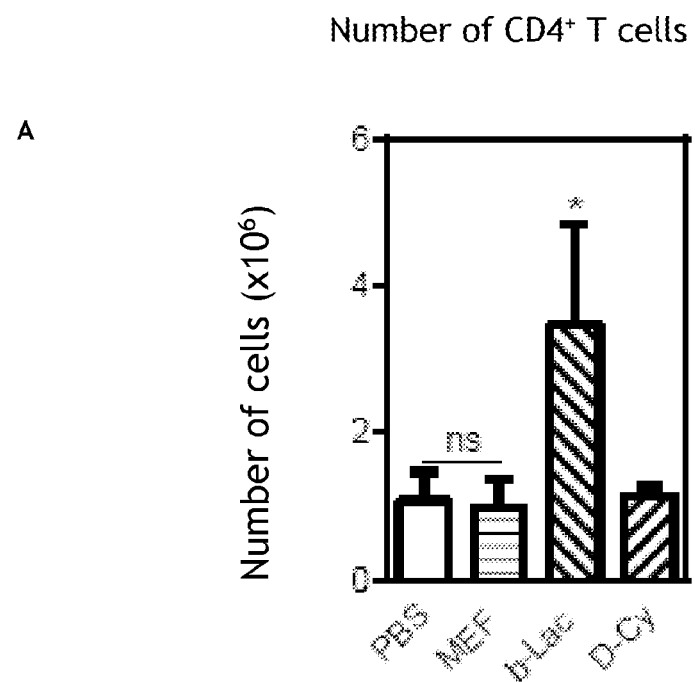
Figure 9:
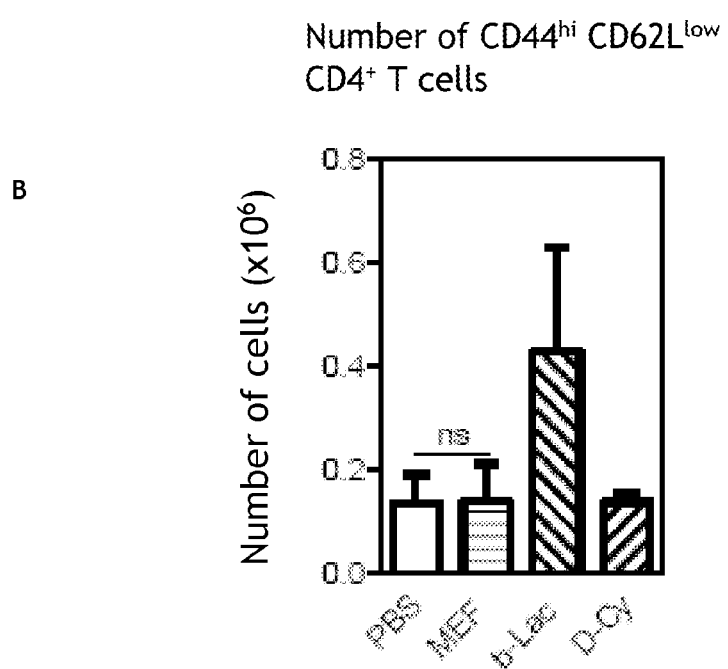
Figure 9:
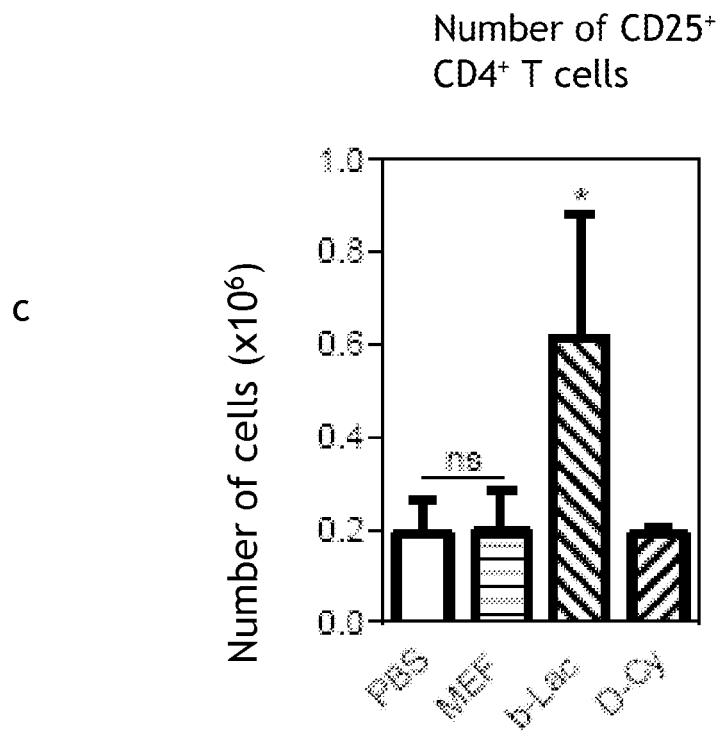
Figure 9:
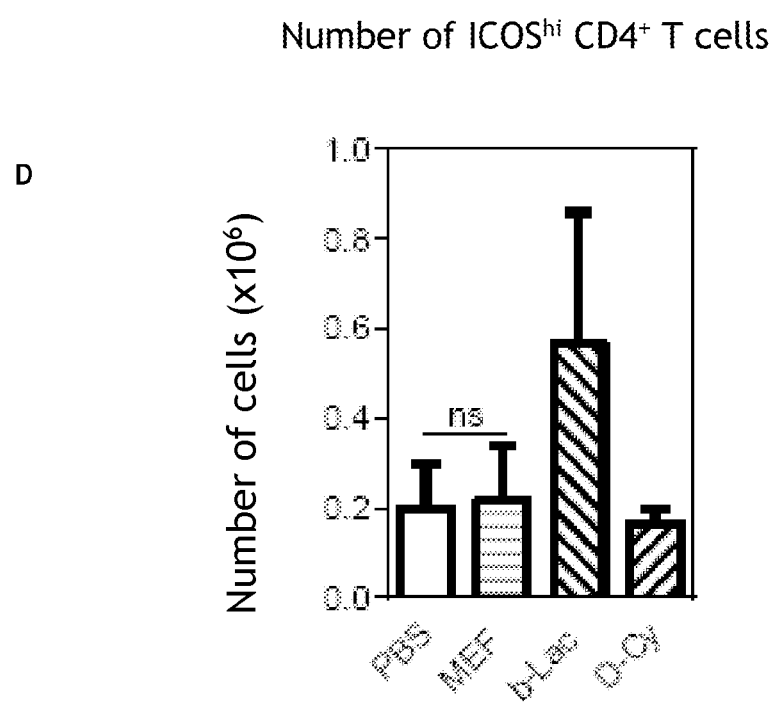
Figure 9:
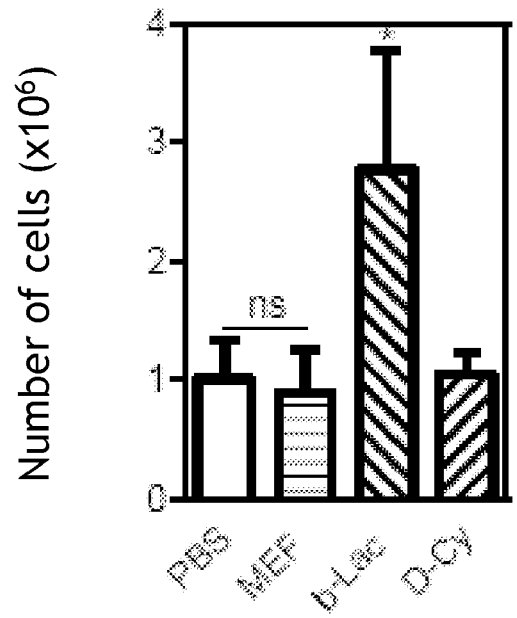
Figure 9:
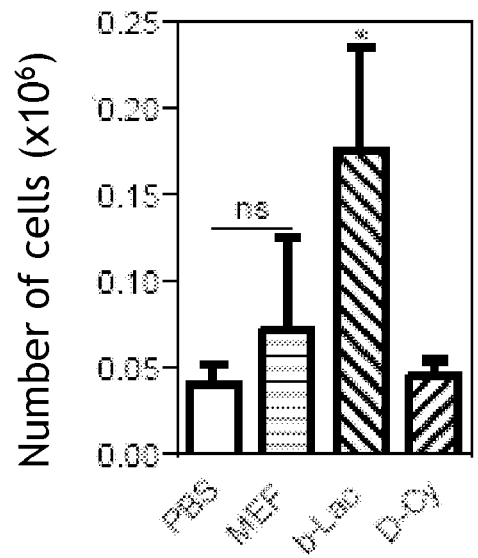

FIG. 9: Total number of lymph node CD4+ T and CD8+ T lymphocytes and number activated after complete immunization with the vaccine forms and one-week post-intravaginal infection with *Chlamydia muridarum*. The total number of CD4+ (A) and CD8+ (E) T lymphocytes and the activation profile thereof are represented here with a focus on the CD4+ CD25+ (C) and ICOS+ (D) lymphocyte population, and on the number of CD44$^{hi}$ CD62L$^{low}$ CD4+ T and CD8+ T lymphocytes (B and F respectively). Graphs representative of an experiment on groups of animals tested individually (PBS, n=3; MEF, n=4; b-Lac, n=5; Dc, n=5). Means±SEM. Unpaired t-test: the symbols *, **, represent measurements of p-values derived from tests carried out with respect to the control MEF (*p≤0.05, **p≤0.01). The symbol "ns" or the absence of stars indicates the absence of statistically significant differences between the group of control animals immunized with sonicate of uninfected MEF cells and the group of control animals injected with PBS alone, or between MEF and b-Lac, or MEF and Dc groups.

Figure 10:
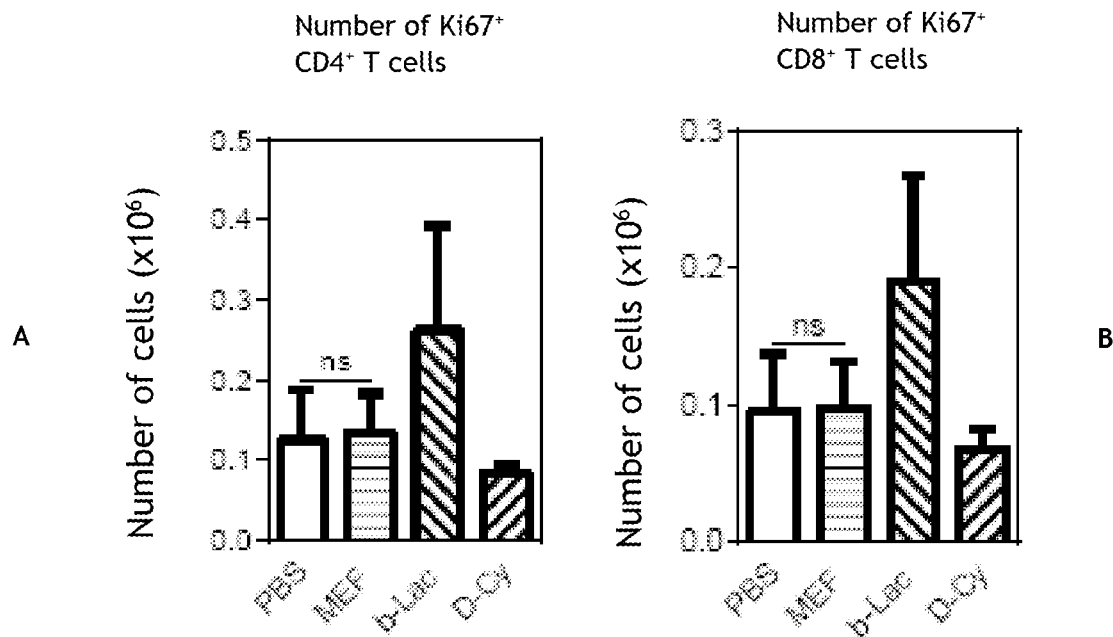
Figure 10:
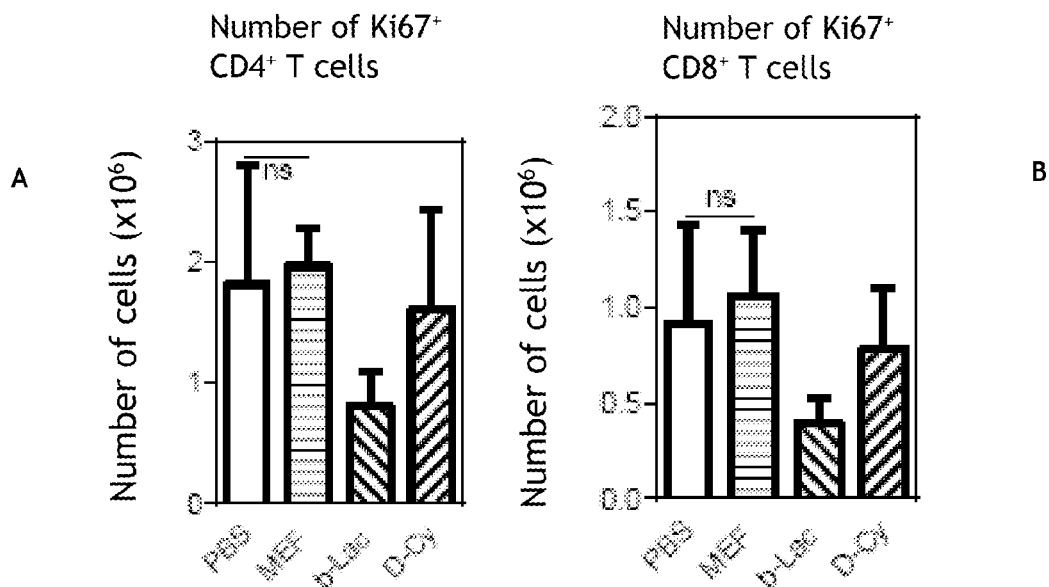

FIG. 10: The number of CD4+ T and CD8+ T lymphocytes proliferating in the lymph nodes draining the genital tract and the spleen after complete immunization with the vaccine forms and one-week post-intravaginal infection with *Chlamydia muridarum*. The total number of CD4+ (A) and CD8+ (B) T lymphocytes proliferating in the lymph nodes draining the genital tract (I) and the spleen (II) is presented here. Graphs representative of an experiment on groups of animals tested individually (PBS, n=3; MEF, n=4; b-Lac, n=5; Dc, n=5). Means±SEM. Unpaired t-test: The symbol "ns" or the absence of stars indicates the absence of statistically significant differences between the group of control animals immunized with sonicate of uninfected MEF cells and the group of control animals injected with PBS alone, or between MEF and b-Lac, or MEF and Dc groups.

Figure 11:
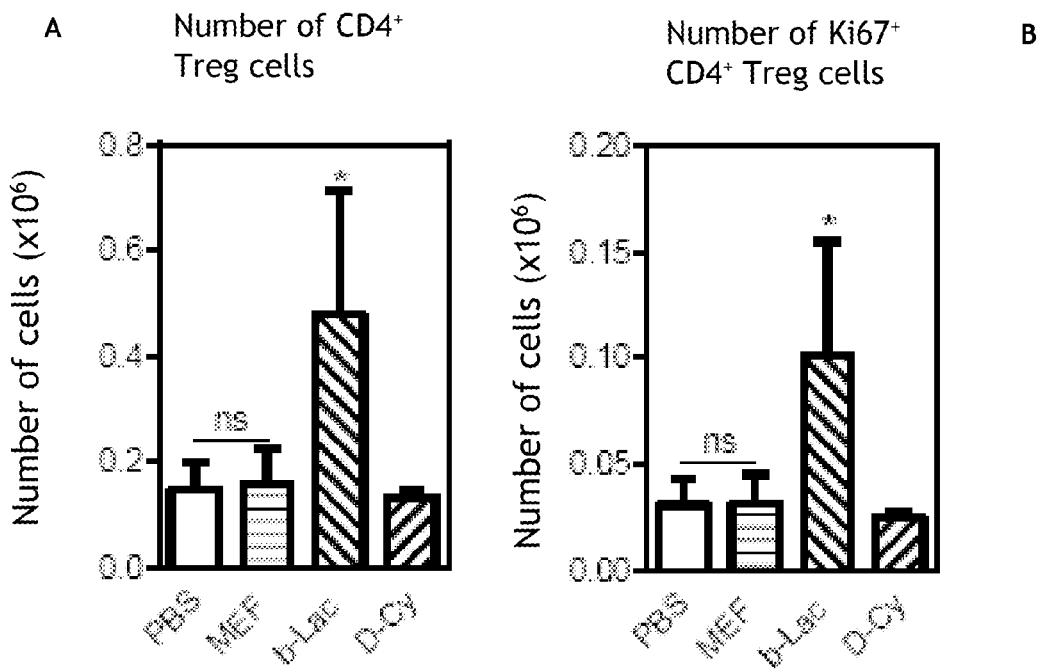
Figure 11:
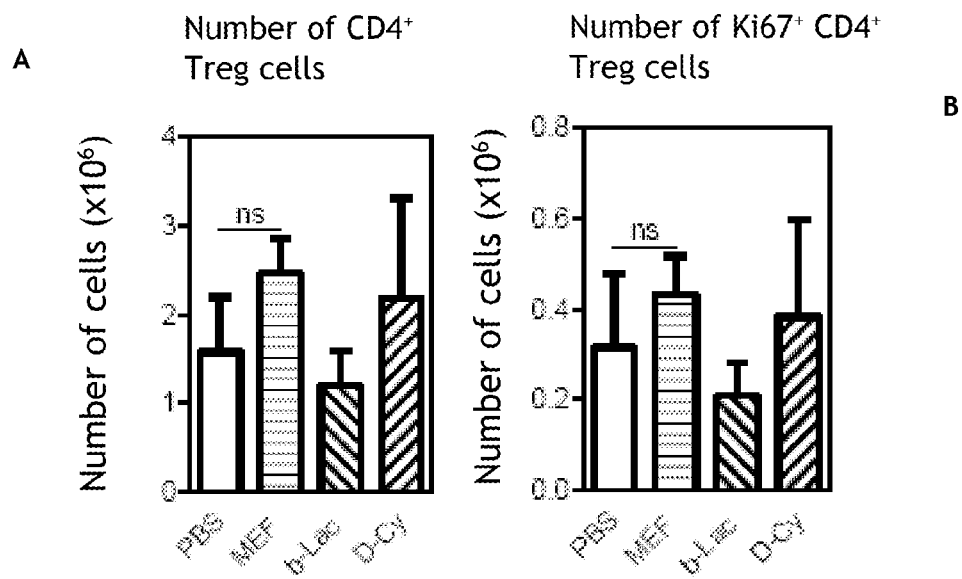

FIG. 11: Total number of CD4+ regulatory T lymphocytes and number proliferating in the lymph nodes draining the genital tract and the spleen after complete immunization with the vaccine forms and one-week post-infection. The total number of CD4+ regulatory T lymphocytes (Treg) (A) and the number proliferating (B) in the lymph nodes draining the genital tract (I) and the spleen (II) are presented here. Graphs representative of an experiment on groups of animals tested individually (PBS, n=3; MEF, n=4; b-Lac, n=5; Dc, n=5). Means±SEM. Unpaired t-test: the symbols represent measurements of p-values derived from tests carried out with respect to the control MEF (*p≤0.05). The symbol "ns" or the absence of stars indicates the absence of statistically significant differences between the group of control animals immunized with sonicate of uninfected MEF cells and the group of control animals injected with PBS alone, or between MEF and b-Lac, or MEF and Dc groups.

EXAMPLES

Example 1: Immunization of C57BL/6J Mice

C57BL/6J mice were vaccinated with different compositions, then secondarily infected with bacteria of the family Chlamydiaceae.

In order to avoid a host immune reaction related to the recognition of alloantigens carried by eukaryotic cells, the various bacterial forms (infectious, BL) were produced in embryonic fibroblasts derived from C57BL/6J mice.

To that end, embryonic fibroblasts (MEF) derived from C57BL/6 mice with *Chlamydia muridarum* (Cm) were infected in vitro. This strain is genetically very similar to *Chlamydia trachomatis*. It infects mice and guinea pigs but not humans, and causes the same physiopathological after-effects in the genital tract as in humans.

Several compositions were prepared
  C1—composition comprising an infectious form of Cm, also called virulent form (72-hour in vitro cell infection and sampling of the cell lysate)
  C2—composition comprising an infectious form inactivated 30 min at 56° C., also called heated form (idem 1 followed by a heat-inactivation step)
  C3—composition comprising an antibiotic-inactivated form: (3-hour in vitro cell infection, then continuous incubation of the infected cells with penicillin G (100 IU/mL), sampling of the cell lysate after 90 hours). This is a BL form and, in particular, a b-Lac form.

It was confirmed by titration that form 1 was infectious, and that forms 2 and 3 were not.

4 groups of 8-week-old female C57BL/6J mice were used.

Three groups were injected via the intraperitoneal (IP) route one or more times with one of the compositions, then the 4 groups were infected via the vaginal route with the infectious form of Cm.

The amount of composition used for each injection corresponded to about 10 cm² of cells (MEF) cultivated in vitro, 100% infected, in a 150 µL volume by IP injection.

group 1 (4 animals): infection with Cm (1 million IFU).
group 2 (3 mice): one IP injection (at time to) of form 1 of the bacterium. At t0+39 d, vaginal infection with 1 million IFU of Cm.
group 3 (3 mice): three IP injections (to, to +10 d, to +21 d) of form 2 of the bacterium. At t0+39 d, vaginal infection with 1 million IFU of Cm.
group 4 (4 mice): three IP injections (to, to +10 d, to +21 d) of form 3 of the bacterium. At t0+39 d, vaginal infection with 1 million IFU of Cm.

After infection, the mice were kept isolated for 82 days, with no antibiotic treatment, in order to allow the physiopathological after-effects to develop. The mice were then sacrificed and examined: macroscopic appearance of the genital tract, investigation of tissue lesions (hydrosalpinx, deformations, fluid cysts), measurement of the weight of the spleen, sampling of various organs (including the para-aortic lymph nodes draining the uterus) for subsequent analyses.

Results obtained:
Group 1: 3/4 of the mice had tissue lesions of the upper genital tract on at least one of the two uterine horns (spleen 106±3 g, normal para-aortic lymph nodes)
Group 2: 1/3 of the mice had tissue lesions of the upper genital tract on at least one of the two uterine horns (spleen 114±9 g, normal para-aortic lymph nodes)
Group 3: 2/3 of the mice had tissue lesions of the upper genital tract on at least one of the uterine horns (spleen 280±81 g, normal para-aortic lymph nodes). One mouse was sacrificed 60 d post-infection because it exhibited skin wounds and substantial weight loss, potentially unrelated to the experiment.
Group 4: no mouse had tissue lesions of the upper genital tract (spleen 111±17 g, normal para-aortic lymph nodes)

This preliminary study shows that only the group of mice preinjected with the BL form of Cm was protected from developing tissue lesions of the upper genital tract, following infection with Cm.

Example 2: Vaccine Efficacy of the BL Forms

In order to confirm the vaccine efficacy of the BL forms, a new experiment was carried out under the same conditions as in example 1.

Mice 1-10: immunization with MEFs at D0, D10 and D21
  Mice 1-5: infection with 2·10⁶ IFU at D39
    3/5 mice (60%) exhibit after-effects (tissue lesions of the upper genital tract)
  Mice 6-10: infection with 2·10⁵ IFU at D39
    3/5 mice (60%) exhibit after-effects (tissue lesions of the upper genital tract)
Mice 11-20: immunization with the infectious form first inactivated 10 min at 90° C. at D0, D10 and D21
  Mice 11-15: infection with 2·10⁶ IFU at D39
    3/5 mice (60%) exhibit after-effects (tissue lesions of the upper genital tract)
  Mice 16-20: infection with 2·10⁵ IFU at D39
    3/5 mice (60%) exhibit after-effects (tissue lesions of the upper genital tract)
Mice 21-30: immunization with the BL form at D0, D10 and D21
  Mice 21-25: infection with 2·10⁶ IFU at D39
    0/5 mice (0%) presents after-effects (tissue lesions of the upper genital tract)
  Mice 26-30: infection with 2·10⁵ IFU at D39
    0/5 mice (0%) presents after-effects (tissue lesions of the upper genital tract)
Mice 31-40: immunization with the infectious form Cm at D0, D10 and D21
  Mice 31-35: infection with 2·10⁶ IFU at D39
    2/5 mice died one-week post-infection
    2/3 surviving mice exhibit after-effects (tissue lesions of the upper genital tract
  Mice 36-40: infection with 2·10⁵ IFU at D39
    2/5 mice died one-week post-infection
    2/3 surviving mice exhibit after-effects (tissue lesions of the upper genital tract)

The results show a significant decrease in the number of infected mice in the group first immunized with the BL form (FIG. 1). These results confirm that the administration of the BL form protects the mice from infection with *C. muridarum*.

Example 3: Effect of Intraperitoneal Injection of Various Immunizing Doses of b-Lac Forms (BL Forms, Treated with a ß-Lactam) or Dc Forms (BL Forms Treated with D-Cycloserine) of *Chlamydia muridarum* on Protection Against Vaginal Infection with *C. muridarum* and the Development of Tubal Pathology 4 groups of 10 female mice were immunized via intraperitoneal injection at D0, D0+10, D0+21 either with an extract of embryonic fibroblasts of C57/BL6 mice (Mefs), or with the b-Lac form (b-Lac), or with the Lac form diluted to one-third of the usual dose (b-Lac/3), or with the Dc form (Dc). These vaccine forms were produced in Mefs.

At D32, the animals were cycled by subcutaneous injection of 50 μL of Deprovera (50 mg/mL, Pfizer).

At D39 the animals were infected via the vaginal route with $10^7$ IFU of *Chlamydia muridarum.*

At D3, D6, D8, D10 and D13 post-infection, vaginal smears were carried out and the presence of *Chlamydia muridarum* was evaluated by titration of the infectious capacity of the Chlamydiae extracted from these smears (FIG. 2).

At 8-weeks post-infection the remaining animals (n=6) were sacrificed, the uterine horns dissected and macroscopic lesions (fluid cysts and translucent zones on the uterine horns or the oviduct) were investigated with the binocular magnifier. Only the mice of the b-Lac group have no macroscopic lesions. The uterine horns were fixed with paraformaldehyde, dehydrated and imbedded in paraffin. Longitudinal sections were stained with HPS (hematoxylin, phloxine, saffron) to show the various structures of the uterine horn (myometrium and endometrium comprising the epithelium and the lamina propria). We evaluated the severity of microscopic damage by the cell loss observed in the uterine lamina propria (FIG. 3).

A larger number of animals with minor tubal lesions (grade 1) or no lesions (grade 0) is observed in the b-Lac and Dc groups, compared with the Mefs and b-Lac/3 groups. The most severe damage visible in the Mefs group is absent in the b-Lac, b-Lac/3 and Dc groups.

These results thus confirm the protective effect of 3 intraperitoneal injections of b-Lac forms (with a confirmed dose-effect) and of Dc forms, with respect to vaginal infection with a virulent form of *Chlamydia muridarum*. This protection is expressed as a reduction in bacterial load from the beginning of the local infection, a specific antibody response which is detectable in the spleen of infected immunized mice, and a protection against inflammatory genital lesions post-infection in these same mice.

Example 4: Study of Lymphocyte Activation after Complete Immunization Followed or not Followed by Infection 1. T Lymphocyte Activation Profile after Complete Immunization with the b-Lac and Dc Vaccine Forms In Vivo One week after complete immunization (three immunizations one week apart), the splenocytes of individual mice were harvested as previously described and the $CD4^+$ and $CD8^+$ T lymphocyte activation profile was studied by flow cytometry with a focus on expression of the classical activation markers CD25, CD62L, CD44 and ICOS. The $CD4^+$ T or $CD8^+$ T lymphocyte population selection (gating) strategy employed was as follows: FSC/SSC (scattering of light emitted at small angles and at 90°), Singlets (elimination of cell doublets), CD19 negative (exclusion of B lymphocytes), $CD3^+$ (selection of T lymphocytes bearing a TCR) then $CD4^+$ ($CD4^+$ T lymphocytes) or $CD8^+$ ($CD8^+$ T lymphocytes). The study of the number of $CD4^+$ regulatory T lymphocytes (Treg) was carried out after permeabilization of the splenocytes and intracellular staining of the FoxP3 molecule. The $CD4^+$ regulatory T lymphocyte (Treg) gating strategy employed was as follows: FSC/SSC, Singlets, CD19 negative (exclusion of B lymphocytes), Fixable Viability $Dye^+$ (selection of viable cells), $CD3^+$ (T lymphocytes), $CD4^+$ ($CD4^+$ T lymphocytes) then $FoxP3^+$ (selection of Tregs, a high expression of FoxP3 being a specific marker of Tregs). Statistical analyses were carried out using the GraphPad PRISM software.

In the spleen, the numbers of total lymphocytes or of CD4+ or CD8+ T lymphocytes are not significantly different between the various groups (FIGS. 4, 5A, 6A). However, the number of $CD44^{hi}$ $CD62L^{low}$ $CD4^+$ activated T lymphocytes is significantly increased following immunization with the b-Lac vaccine form alone (FIG. 35). The expression profile of ICOS on the $CD4^+$ T lymphocytes also shows a very significant increase in the number of $ICOS^+$ $CD4^+$ T lymphocytes (ICOS being a marker reflecting the inflammatory potential of $CD4^+$ lymphocytes) (FIG. 5). In parallel, FoxP3 intracellular staining shows a decrease in the $CD4^+$ regulatory lymphocyte population, significant in terms of number following immunization with the Dc vaccine form. The same trend is observed in the b-Lac group (FIG. 5E). The vaccine forms do not induce significant differences in terms of $ICOS^+$ $CD8^+$ T populations (FIG. 6B). A significant increase in the number of $CD44^{hi}$ $CD62L^{low}$ $CD8^+$ activated T lymphocytes is noted after immunization with the b-Lac form (FIG. 6C).

2. T Lymphocyte Activation Profile after Complete Immunization with the b-Lac and Dc Vaccine Forms Followed by Intravaginal Infection with $10^7$ IFU of *Chlamydia muridarum.*

After complete immunization (three immunizations one week apart), the mice were cycled by injection of progesterone (Deprovera, 50 µL per mouse) and infected with $10^7$ IFU of *Chlamydia muridarum* via the intravaginal route. After one-week post-infection, the mice were sacrificed and tested individually. The splenocytes and lymph nodes draining the genital tract (inguinal/para-aortic/mesenteric) were harvested and isolated. The activation profile and the number of $CD4^+$ and $CD8^+$ T lymphocytes were studied by flow cytometry as indicated in the preceding paragraph (part 1) with a focus on expression of CD25, CD62L, CD44 and ICOS. The study of T lymphocyte proliferation and number of Tregs is carried out after permeabilization and intracellular staining of the molecule Ki67 (proliferation) and FoxP3 (Treg). Statistical analyses were carried out using the GraphPad PRISM software.

FIG. 7 presents the total number of lymphoid cells of the lymph nodes draining the genital tract and the spleen of the mice of the 4 groups PBS, MEF, b-Lac or Dc. It is quite clear that immunization with the b-Lac form followed by intravaginal infection of the mice leads to a clear increase in the number of lymphocytes of the draining lymph nodes $p \leq 0.05$) and also a quite marked decrease in the spleen $p \leq 0.01$).

In the spleen of these mice, one also observes, for the b-Lac group, a significant decrease in CD4+ CD25+ T lymphocytes (FIG. 8B) and a comparable trend for the $CD44^{hi}$ $CD62L^{low}$ CD4+ and CD4+ T lymphocytes (FIGS. 8A and 8C, respectively) With regard to the CD8+ T lymphocytes, in the b-Lac group, they are significantly decreased ($p \leq 0.05$, FIG. 8D), as well as the CD8+CD25+ T $p \leq 0.01$, FIG. 8E).

A mirror image is observed in the draining lymph nodes, with a significant increase in the same CD4+ and CD4+ CD25+ T populations (FIGS. 9A and C) in the b-Lac group, and a comparable trend for the CD4+ and $CD44^{hi}$ $CD62L^{low}$ CD4+ and CD4+ $ICOS^{hi}$ T lymphocytes (FIGS. 9B and D). The same observation applies to the CD8+ and $CD44^{hi}$ $CD62L^{low}$ CD8+ T lymphocytes, which are also significantly increased only in the b-Lac group (FIGS. 9 E and F).

Consistent with the results above, if the numbers of proliferating (carrying the nuclear marker Ki67) CD4+ and CD8+ T lymphocytes are examined, a clear trend toward a decrease in the spleen and an increase in the lymph nodes is observed, again only in the b-Lac group (FIG. 10).

Analyses of the number of regulatory T lymphocytes (carrying markers CD4 and FoxP3) arrive at the same conclusions, again in the b-Lac group: trend toward a decrease in CD4+ Ki67+ Treg in the spleen, and significant increases $p \leq 0.05$) of CD4+ and CD4+ Ki67+ T reg in the draining lymph nodes (FIG. 11).

All of these results suggest that the immunizing injections of b-Lac forms induce an activation and a T immune response specific for *Chlamydia muridarum* in the spleen, with production of specific antibodies. In response to intravaginal infection, the activated T lymphocytes leave the spleen for the lymph nodes draining the genital tract. Thus, an immune basis for the drop in local bacterial load (effector lymphocytes) and for the reduction in the local inflammatory reaction generating tissue lesions (regulatory T-lymphocytes) is provided.

The invention claimed is:

1. A method of treating infections caused by *Chlamydia* bacteria selected in the group consisting of *Chlamydia muridarum, Chlamydia pneumoniae, Chlamydia psitacci, Chlamydia abortus, Chlamydia felis, Chlamydia caviae, Chlamydia pecorum, Chlamydia suis* and *Chlamydia trachomatis*, comprising:

administering to a subject in need thereof a composition comprising a therapeutically effective amount of an inactivated BL form of *Chlamydia* bacteria selected from the group consisting of *Chlamydia muridarum, Chlamydia pneumoniae, Chlamydia psitacci, Chlamydia abortus, Chlamydia felis, Chlamydia caviae, Chlamydia pecorum, Chlamydia suis* and *Chlamydia trachomatis,* wherein the inactivated BL form of *Chlamydia* bacteria has been previously inactivated by treating with a β-lactam, wherein the β-lactam is selected from the group consisting of amoxicillin, benzylpenicillin, phenoxymethylpenicillin, cloxacillin, cefadroxil, cefixime, imipenem, mecillinam, clavulanic acid, tazobactam, sulbactam, and the combination of cefixime and imipenem.

2. The method of claim 1, wherein said β-lactam is penicillin G.

3. The method of claim 1, wherein *Chlamydia* bacteria is *Chlamydia trachomatis* or *Chlamydia muridarum.*

4. The method of claim 1, wherein a pathology caused by the infection with *Chlamydia* bacteria is an ocular pathology, a genital pathology, a respiratory pathology, a cardiovascular dysfunction, a circulatory dysfunction, a joint disease, or an inflammatory disease.

5. The method of claim 4, wherein said genital pathology is selected from the group consisting of venereal lymphogranuloma, urethritis, orchiepididymitis, cervicovaginitis, cervicitis, endocervicitis, endometritis, perihepatitis and salpingitis.

* * * * *